US005948903A

United States Patent [19]
Cook et al.

[11] Patent Number: 5,948,903
[45] Date of Patent: Sep. 7, 1999

[54] SYNTHESIS OF 3-DEAZAPURINES

[75] Inventors: P. Dan Cook, Carlsbad; Oscar L. Acevedo, San Diego; Robert S. Andrews, San Juan Capistrano, all of Calif.

[73] Assignee: ISIS Pharmaceuticals, Inc., Carlsbad, Calif.

[21] Appl. No.: 09/074,503

[22] Filed: May 8, 1998

Related U.S. Application Data

[60] Continuation of application No. 08/762,588, Dec. 10, 1996, Pat. No. 5,750,692, which is a division of application No. 08/514,762, Aug. 14, 1995, Pat. No. 5,587,470, which is a division of application No. 08/027,011, Mar. 4, 1993, Pat. No. 5,380,429, which is a continuation-in-part of application No. PCT/US91/00243, Jan. 11, 1991.

[51] Int. Cl.$^6$ .............................. C07H 19/04; C07H 21/00
[52] U.S. Cl. ..................................... 536/25.34; 536/25.33; 536/26.7; 536/27.13; 536/27.3; 536/27.6; 536/27.7; 544/242; 544/245; 544/253; 544/278; 544/279; 546/118
[58] Field of Search ............................... 536/27.13, 27.3, 536/27.6, 27.7, 25.34, 25.33, 26.7; 544/253, 242, 245, 278, 279; 546/118

[56] References Cited

U.S. PATENT DOCUMENTS

| 3,919,193 | 11/1975 | Mian et al. . |
|---|---|---|
| 4,318,344 | 4/1983 | Rideout et al. . |
| 4,481,195 | 11/1984 | Rideout et al. . |
| 5,457,191 | 10/1995 | Cook et al. . |
| 5,587,470 | 12/1996 | Cook et al. . |
| 5,750,692 | 5/1998 | Cook et al. . |

FOREIGN PATENT DOCUMENTS

WO 91/10671  7/1991  WIPO .

OTHER PUBLICATIONS

Atherton et al., "The Peptides", Gross and Meienhofer, Eds., Academic PRess, NY, 1983, vol. 9, pp. 1–38.

Beaucage et al., "Deoxynucleoside Phosphoramidites—A New Class of Key Intermediates for Deoxypolynucleotide Synthesis", *Tetrahedron Letters*, 1981, 22, 1859–1862.

Beaucage, "3H–1, w–Benzodithiol–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1255.

Burman et al., "IV: Studies on Biological Activities and Mechanism of Action 3–deazaguaine Nucleosides", *Chem. Scripta*, 1986, 26, 155–159.

Caruthers, "Synthesis of Oligonucleotides and Oligonucleotide Analogues, Oligodeoxynucleotides", Cohen (ed.), CRC Press, Inc., Boca Raton, FL, 1989.

"The Chemistry of Heterocyclic Compounds", Weissberger, A. (ed.), Imidazole and Derivatives, Part 1, Interscience, NY, 1953.

Cook et al., "Synthesis of 3–deazaguanine, 3–deazaguanosine, and 3–deazaguanylic Acid by a Novel Ring Closure of Imidazole Precursors", *J. Am. Chem. Soc.*, 1975, 97, 2916.

Cook et al., "Synthesis and Antiviral and Enzymatic Studies of Certain 3–Deazaguaines and Their Imidazolecarboxamide Precursors", *J. Med. Chem.*, 1978, 21, 1212.

Cook et al., "Synthesis of 7– and 9–β–D–Ribofuranosides of 3–Deaza–6–thioguanine and 3–Deaza–2, 6–diaminopurine by a Novel Ring CLosure of 4(5)–Cyano–5(4)–cyanomethylimidazole β–D–Ribofuranosides", *J. Org. Chem.*, 1978, 43, 289.

Greene and Wuts, "Protective Groups in Organic Synthesis", 2nd Edition, John Wiley & Sons, New York, 1991.

Hartman et al, "Synthesis of [2–$^{14}$C] Dezaguaine Mesylate (6–Amino–1,5–Dihydro–4h–[Midazo[4,5$_{-6}$] Pyridin–4–One–y–$^{14}$C Methanesultonate), A New Antitumor Agent", *J. Labelled Compd. Radiopharm.*, 1985, 23, 35.

*J. Medicinal Chem.*, 1984, 27, 1389.

*J. Medicinal Chem.*, 1978, 21, 1212.

Loose–Mitchell, "Antisense Nucleic Acids as a Potential Class of Pharmaceutical Agents", *TIPS*, 1988, 9, 45–47.

Marcus–Sekura, "Techniques for Using Antisense Oligodeoxyribonucleotides to Study Gene Expression", *Anal. Biochemistry*, 1988, 172, 289–295.

Miles et al., "A Conformational Basis for the Selective Action of Ara–Adenine", *J. Theor. Biol.*, 1977, 67, 499.

Miller et al., "A New Approach to Chemotherapy Based on Molecular Biology and Nucleic Acid Chemistry: Matagen (Masking Tape for Gene Expression", *Anti–Cancer Drug Design*, 1987, 2, 117–128.

Motawai, M.S. et al., "A New route to 2', 3'–Dideoxycytidine", *Liebigs Ann. Chem.*, 1990, 599–602.

Pretsch et al., "Spectral Data for Structure Determination of Organic Compounds", 2nd edition, 1989, P. H–15.

Revankar et al, "Synthesis and Antiviral/Antitumor Activities of Certain 3–Deazaguaine Nucleosides and Nucleotides", *J. Med. Chem.*, 1984, 27, 1389.

(List continued on next page.)

*Primary Examiner*—James O. Wilson
*Attorney, Agent, or Firm*—Woodcock Washburn Kurtz Mackiewicz & Norris LLP

[57] ABSTRACT

This invention relates to compounds based on the 3-deazapurines ring system and to methods for making such compounds. The invention also generally relates to the field of "antisense" agents, agents that are capable of specific hybridization with a nucleotide sequence of an RNA. The 3-deazapurine-containing compounds of this invention can be useful for modulating the activity of RNA when incorporated into oligonucleotides. Oligonucleotides and their analogs are used for a variety of therapeutic and diagnostic purposes, such as treating diseases, regulating gene expression in experimental systems, assaying for RNA and for RNA products through the employment of antisense interactions with such RNA, diagnosing diseases, modulating the production of proteins and cleaving RNA in site specific fashions.

25 Claims, No Drawings

OTHER PUBLICATIONS

Rosenmeyer et al., "Syn–Anti Conformational Analysis of Regular and Modified Nucleosides by ID $^1$H NOE Difference Spectroscopy: A Simple Graphical Method Based on Conformationally Rigid Molecules", *J. Org. Chem.*, 1990, 55, 5784.

Saenger, "Principles of Nucleic Acid Structure", Cantor, C.R. (ed.), Springer–Verlag, New York, 1983.

Saran et al., "Molecular Orbital Studies on the Structure of Nucleoside Analogs. IV. Conformation of 3–Deazapurine Nucleosides", *Int. J. Quantum Chem.*, 1984, 25, 743.

Stein et al., "Oligodeoxynucleotides as Inhibitors of Gene expression: A Review", *Cancer Research*, 1988, 48, 2659–2668.

Stein et al., "Physiochemical Properties of Phosphorothioate Oligodeoxynucleotides", *Nucleic Acids Res.*, 1988, 16, 3209–3221.

Van der Krol et al., "Modulation of Eukaryotic Gene Expression by Complementary RNA or DNA Sequences", *BioTechniques*, 1988, 6, 958–973.

Veber and Hirschmann et al.,"Isonicotinyloxycarbonyl, a Novel Amino Protecting Group for Peptide Synthesis", *J. Org. Chem.*, 1977, 42, 3286.

Walder, "Antisense DNA and RNA: Progress and Prospects", *Genes & Development*, 1988, 2, 502–504.

Walder et al., "Role of RNase H in Hybrid–Arrested Translation by Antisense Oligonucleotides", *PNAS USA*, 1988, 85, 5011–5015.

Zon, "Synthesis of Backbone–Modified DNA Analogues for Biological Applications", *J. Protein Chemistry*, 1987, 6, 131–145.

Zon, "Oligonucleotide Analogues as Potential Chemotherapeutic Agents", *Pharmaceutical Res.*, 1988, 5, 539–549.

Offensperger, W. et al., "In vivo Inhibition of Duck Hepatitis B Virus Replication and Gene Expression by Phosphorothioate Modified Antisense Oligodeoxynucleotides", *EMBO J.*, 1993, 12(3), 1257–1262.

Simons, M. et al., "Antisense c–myb Oligonucleotides Inhibit Intimal Arterial Smooth Muscle Cell Accumulation in vivo", *Nature*, 1992, 359, 67–70.

Burch, R. and Mahan, "Oligonucleotides Antisense to the Interleukin 1 Receptor mRNA Block the Effects of Interleukin 1 in Cultured Murine and Human Fibroblasts and in Mice", *J. Clinical Investigation*, 1991, 88, 1190–1196.

Kitajima, I. et al., "Ablation of Transplanted HTLV–I Tax–Transformed Tumors in Mice by Antisense Inhibition of NF–κB", *Science*, 1992, 258, 1792–1795.

Higgins, K. et al., "Antisense Inhibition of the p65 Subunit of NF–κB Blocks Tumorigenictiy and Causes Tumor Regression", *PNAS USA*, 1993, 90, 9901–9905.

Vlassov, V., "Inhibition of Tick–Borne Viral Encephalitis Expression Using Covalently Linked Oligonucleotide Analogs", in "Oligodeoxynucleotides as Antisense Inhibitors of Gene Expresison: Therapeutic Implications", Jun. 18–21, 1989, Rockville, MD.

Sambrook, J. et al. (eds.), "Molecular Cloning A Laboratory Manual", Cold Spring Harbor Laboratory Press, 1989.

"Antisense Antiviral Drug in Clinical Trials", *Antiviral Agents Bulletin*, Jun. 1992, 5(6), 161–163.

*BioWorld Today*, Dec. 20, 1993, 3.

SYNTHESIS OF 3-DEAZAPURINES

RELATED APPLICATIONS

This application is a continuation of U.S. patent application Ser. No. 08/762,588, filed on Dec. 10, 1996 now U.S. Pat. No. 5,750,692, which is a divisional of U.S. patent application Ser. No. 08/514,762, filed on Aug. 14, 1995 now U.S. Pat. No. 5,587,470, which is a division of U.S. patent application Ser. No. 08/027,011, filed on Mar. 4, 1993 now U.S. Pat. No. 5,380,429, which is a continuation-in-part of International Patent Application PCT\US91\00243, filed Jan. 11, 1991, published as WO 91/10671 on Jul. 25, 1991.

BACKGROUND OF THE INVENTION

This invention relates to compounds that have utility as oligonucleotide intermediates, and to methods for making such compounds. The compounds are based on the 3-deazapurine core. The invention also generally relates to the field of "antisense" agents, agents that are capable of specific hybridization with a nucleotide sequence of an RNA. In particular, this invention relates to novel compounds that may be incorporated into oligonucleotides, these compounds include novel heterocyclic bases, nucleosides, and nucleotides. When incorporated into oligonucleotides, the 3-deazapurines of the invention can be useful for modulating the activity of RNA. Oligonucleotides are used for a variety of therapeutic and diagnostic purposes, such as treating diseases, regulating gene expression in experimental systems, assaying for RNA and for RNA products through the employment of antisense interactions with such RNA, diagnosing diseases, modulating the production of proteins, and cleaving RNA in site specific fashions.

It is well known that most of the bodily states in mammals including most disease states, are effected by proteins. Such proteins, either acting directly or through their enzymatic functions, contribute in major proportion to many diseases in animals and man. Classical therapeutics has generally focused upon interactions with such proteins in efforts to moderate their disease causing or disease potentiating functions. Recently, however, attempts have been made to moderate the actual production of such proteins by interactions with molecules that direct their synthesis, intracellular RNA. By interfering with the production of proteins, it has been hoped to effect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. A number of workers have reported such attempts. Pertinent reviews include Stein, et al., *Cancer Research*, 1988, 48, 2659–2668; Walder, *Genes & Development*, 1988, 2, 502–504; Marcus-Sekura, *Anal. Biochemistry*, 1988, 172, 289–295; Zon, *J. Protein Chemistry*, 1987, 6, 131–145; Zon, *Pharmaceutical Res.*, 1988, 5, 539–549; Van der Krol, et al., *BioTechniques*, 1988, 6, 958–973; and Loose-Mitchell, *TIPS*, 1988, 9, 45–47. Each of the foregoing provide background concerning general antisense theory and prior techniques.

Thus, antisense methodology has been directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another.

Prior attempts at antisense therapy have provided oligonucleotides or oligonucleotide analogs that are designed to bind in a specific fashion to—which are specifically hybridizable with—a specific mRNA by hybridization. Such oligonucleotide and oligonucleotide analogs are intended to inhibit the activity of the selected mRNA—to interfere with translation reactions by which proteins coded by the mRNA are produced—by any of a number of mechanisms. The inhibition of the formation of the specific proteins that are coded for by the mRNA sequences interfered with have been hoped to lead to therapeutic benefits.

A number of chemical modifications have been introduced into antisense agents—oligonucleotides and oligonucleotide analogs—to increase their therapeutic activity. Such modifications are designed to increase cell penetration of the antisense agents, to stabilize the antisense agents from nucleases and other enzymes that degrade or interfere with their structure or activity in the body, to enhance the antisense agents' binding to targeted RNA, to provide a mode of disruption (terminating event) once the antisense agents are sequence-specifically bound to targeted RNA, and to improve the antisense agents' pharmacokinetic and pharmacodynamic properties. These modifications are designed to enhance the uptake of antisense agents—oligonucleotides and oligonucleotide analogs—and thus provide effective therapeutic, research reagent, or diagnostic uses.

Initially, only two mechanisms or terminating events have been thought to be operating in the antisense approach to therapeutics. These are the hybridization arrest mechanism and the cleavage of hybridized RNA by the cellular enzyme, ribonuclease H (RNase H). It is likely that additional "natural" events may be involved in the disruption of targeted RNA, however. These naturally occurring events are discussed by Cohen in *Oligonucleotides: Antisense Inhibitors of Gene Expression*, CRC Press, Inc., Boca Raton, Fla. (1989).

The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides, Miller, et al., *Anti-Cancer Drug Design*, 1987, 2, 117–128, and α-anomer oligonucleotides are the two most extensively studied antisense agents that are thought to disrupt nucleic acid function by hybridization arrest.

The second "natural" type of terminating event is the activation of RNase H by the heteroduplex formed between the DNA type oligonucleotide or oligonucleotide analog and the targeted RNA with subsequent cleavage of target RNA by the enzyme. The oligonucleotides or oligonucleotide analogs, which must be of the deoxyribose type, hybridize with the targeted RNA and this duplex activates the RNase H enzyme to cleave the RNA strand, thus destroying the normal function of the RNA. Phosphorothioate modified oligonucleotides are the most prominent example of antisense agents that are thought to operate by this type of antisense terminating event. Walder, et al., in *Proceedings of the National Academy of Sciences of the U.S.A.*, 1988, 85, 5011–5015 and Stein, et al., in *Nucleic Acids Research*, 1988, 16, 3209–3221 describe the role that RNase H plays in the antisense approach.

To increase the potency via the "natural" termination events the most often used oligonucleotide modification is modification at the phosphorus atoms. An example of such modifications include methyl phosphonate oligonucleotides, where the phosphoryl oxygen of the phosphorodiester linking moiety is replaced or the nucleotide elements together are replaced, either in total or in part, by methyl groups. Other types of modifications to the phosphorus atom of the phosphate backbone of oligonucleotides include phosphorothioate oligonucleotides. The phosphorothioate modified oligonucleotides are thought to terminate RNA by activation of RNase H upon hybridization to RNA although hybridization arrest of RNA function may play some part in their activity. Backbone modifications are disclosed as set forth in U.S. patent applications assigned to a common assignee hereof, entitled "Backbone Modified Oligonucleotide Analogs," Ser. No. 07/703,619, now U.S. Pat. No. 5,378,825 and "Heteroatomic Oligonucleotide Linkages," Ser. No. 07/903,160, now abandoned, the disclosures of which are incorporated herein by reference to disclose more fully such modifications. Phosphoroamidites have been disclosed as set forth in an application having U.S. Ser. No. 07/918,362, now U.S. Pat. No. 5,506,351 and assigned to a common assignee hereof, entitled "Improved Process for Preparation of 2'-O-Alkylguanosines and Related Compounds," the disclosures of which are incorporated herein by reference to disclose more fully such modifications.

All applications of oligonucleotides and oligonucleotide analogs as antisense agents for therapeutic purposes, diagnostic purposes, and research reagents require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides and oligonucleotide analogs toward nuclease degradation.

A serious deficiency of unmodified oligonucleotides for these purposes, particularly antisense therapeutics, is the enzymatic degradation of the administered oligonucleotides by a variety of intracellular and extracellular ubiquitous nucleolytic enzymes, hereinafter referred to as "nucleases." It is unlikely that unmodified, "wild type," oligonucleotides will be useful therapeutic agents because they are rapidly degraded by nucleases. A primary focus of antisense research has been to modify oligonucleotides to render them resistant to such nucleases. These modifications have heretofore exclusively taken place on the sugar-phosphate backbone, particularly on the phosphorus atom. Phosphorothioates, methyl phosphonates, phosphoramidites, and phosphorotriesters (phosphate methylated DNA) have been reported to have various levels of resistance to nucleases. Backbone modifications are disclosed as set forth in U.S. patent applications assigned to a common assignee hereof, entitled "Backbone Modified oligonucleotide Analogs," Ser. No. 07/703,619 and "Heteroatomic Oligonucleotide Linkages," Ser. No. 07/903,160, the disclosures of which are incorporated herein by reference to disclose more fully such modifications.

Other modifications to "wild type" oligonucleotides made to enhance resistance to nucleases, activate the RNase terminating event, and enhance the RNA-oligonucleotide duplex's hybridization properties include functionalizing the nucleoside's naturally occurring sugar. Sugar modifications are disclosed as set forth in PCT Application assigned to a common assignee hereof, entitled "Compositions and Methods for Detecting and Modulating RNA Activity and Gene Expression," Ser. No. 07/854,634, now abandoned, the disclosures of which are incorporated herein by reference to disclose more fully such modifications.

Other synthetic terminating events, as compared to hybridization arrest and RNase H cleavage, have been studied in an attempt to increase the potency of oligonucleotides and oligonucleotide analogs for use in antisense diagnostics and therapeutics. Thus, an area of research has developed in which a second domain to the oligonucleotide, generally referred to as a pendant group, has been introduced.

The pendant group is not involved with the specific Watson-Crick hybridization of the oligonucleotide or oligonucleotide analog with the mRNA but is carried along by the oligonucleotide or oligonucleotide analog to serve as a reactive functionality. The pendant group is intended to interact with the mRNA in some manner more effectively to inhibit translation of the mRNA into protein. Such pendant groups have also been attached to molecules targeted to either single or double stranded DNA. Such pendant groups include, intercalating agents, cross-linkers, alkylating agents, or coordination complexes containing a metal ion with associated ligands. A discussion of pendant groups is set forth in PCT Application assigned to a common assignee hereof, entitled "Compositions and Methods for Detecting and Modulating RNA Activity and Gene Expression," U.S. Ser. No. No. 07/854,634, the disclosure of which are incorporated herein by reference in order to disclose more fully such modifications.

Prior approaches using cross-linking agents, alkylating agents, and radical generating species as pendant groups on oligonucleotides for antisense diagnostics and therapeutics have several significant shortcomings. The sites of attachment of the pendant groups to oligonucleotides play an important, yet imperfectly known, part in the effectiveness of oligonucleotides for therapeutics and diagnostics. Prior workers have described most pendant groups as being attached to a phosphorus atom which affords oligonucleotide compositions with inferior hybridization properties. Prior attempts have been relatively insensitive, that is the reactive pendant groups have not been effectively delivered to sites on the messenger RNA molecules for alkylation or cleavage in an effective proportion. Moreover, even if the reactivity of such materials were perfect, (i.e., if each reactive functionality were to actually react with a messenger RNA molecule), the effect would be no better than stoichiometric. That is, only one mRNA molecule would be inactivated for each oligonucleotide molecule. It is also likely that the non-specific interactions of oligonucleotide compositions with molecules other then the target RNA, for example with other molecules that may be alkylated or which may react with radical species, as well as self-destruction, not only diminishes the diagnostic or therapeutic effect of the antisense treatment but also leads to undesired toxic reactions in the cell or in vitro. This is especially acute with the radical species that are believed to be able to diffuse beyond the locus of the specific hybridization to cause undesired damage to non-target materials, other cellular molecules, and cellular metabolites. This perceived lack of specificity and stoichiometric limit to the efficacy of such prior alkylating agent and radical generating-types of antisense oligonucleotide compositions is a significant drawback to their employment.

Reactive functionalities or pendant groups attached to oligonucleotide compositions previously described in the literature have been almost exclusively placed on a phosphorus atom, the 5-position of thymine, and the 7-position of purines. A phosphorus atom attachment site can allow a reactive group access to both the major and minor grooves. However, internal phosphorus modification results in greatly reduced heteroduplex stability. Attachments at the 3' and/or 5' ends are limiting in that only one or two functional groups can be accommodated in the oligonucleotide compositions. Such placement can interfere with Watson-Crick binding. Further, functionalities placed in the 5-position or 7-position of bases, pyrimidine and purine, respectively will reside in the major groove of the duplex and will not be in proximity to the RNA 2'-hydroxyl substrate. The 2'-hydroxyl is the "trigger" point for RNA inactivation, and thus, any reactive functionalities must be in appropriate proximity to the receptive substrate located in the targeted RNA, especially the most sensitive point, the 2'-hydroxyl group.

Targeted RNA is inactivated by formation of covalent links between a modified oligonucleotide and the RNA 2'-hydroxyl group. A variety of structural studies such as X-ray diffraction, chemical reaction, and molecular modeling studies suggests that the 2'-hydroxyl group of RNA in a duplex or heteroduplex resides in the minor groove.

The half life of the perfectly formed duplex will be greatly effected by the positioning of the tethered functional group. Inappropriate positioning of functional groups, such as placement on the Watson/Crick base pair sites, would preclude duplex formation. Other attachment sites may allow sequence-specific binding but may be of such low stability that the reactive functionality will not have sufficient time to initiate RNA disruption.

Approaches to perfect complementation between modified oligonucleotides or oligonucleotides and targeted RNA will result in the most stable heteroduplexes. This is desired because the heteroduplex must have a sufficient half life to allow the reactive or non-reactive functionalities of this invention to initiate the cleavage or otherwise disruption of RNA function. The minor side or minor groove of the duplexes formed between such oligonucleotides or modified oligonucleotides and the targeted RNA has been found to be the greatly preferred site for functional group activity.

Therefore, functionalities placed on sequence-specific oligonucleotide compositions (via modified nucleosides) should preferably reside in the minor groove formed between the oligonucleotide composition and the targeted RNA, not interfere with duplex formation or stability, and initiate cleavage or disruption of the RNA. Accordingly, there remains a great need for antisense oligonucleotide compositions that are capable of improved specificity and effectiveness both in binding and in MRNA modulation or inactivation without the imposition of undesirable side effects.

It has now been found that certain positions on the nucleosides of double stranded nucleic acids are exposed in the minor groove and may be substituted without affecting Watson-Crick base-pairing or duplex stability. Reactive or non-reactive functionalities placed in these positions can best initiate cleavage and destruction of targeted RNA or interfere with its activity.

The functionalities point of attachment to the base units, which in turn may be converted to modified oligonucleotide, is critical in the design of compositions for sequence-specific destruction or modulation of targeted RNA. The functionalities must not interfere with Watson-Crick base pair hydrogen bonding rules, as this is the sequence-specific recognition/binding factor essential for selection of the desired RNA to be disrupted. Further, the functionalities should improve the oligonucleotides compositions' pharmacokinetic and/or pharmacodynamic properties, as well as the oligonucleotide compositions' transport properties across cellular membranes. The present invention addresses these, as well as other, needs by presenting novel oligonucleotide intermediates based on the core structure of 3-deazapurines.

The synthesis of the 3-deazaguanine core is known, Cook, et al., *J. Am. Chem. Society* 1975, 97, 2916; Cook et al., *J. Med. Chem.* 1978, 21, 1212. 3-deazaguanine is a potent guanine antimetabolite with significant antitumor, antiviral, antibacterial and antiparasitic activities. The corresponding nucleoside, 2'-deoxy-3-deazaguanosine, has exhibited a wide spectrum, Revankar, et al., *J. Med. Chem.*, 27, 1389, 1984, of antiviral and antitumor activity in addition to antibacterial activity against *E. coli*, Burman, et al., *Chem. Scripta* 1986, 26, 15. Workers have made certain modifications to 3-deazaguanine (6-aminoimidazo [4,5-c]pyridine) and the corresponding nucleoside 2'-deoxy-3-deazaguanosine (6-amino-1-(2-deoxy-β-D-erythropentofuranosyl))imidazo [4,5-c]pyridin-4(5H)-one resulting in a wide modulation of the heterocyclic ring system's biological activity. See, e.g., Hartman, et al., *J. Labelled Compd. Radiopharm.* 1985, 23, 35 (ring modifications); Revankar, et al., *J. Med. Chem.* 1984, 27, 1389 (peripheral modifications); Cook, et al., *J. Org. Chem.* 1978, 43, 289 (same); Revankar, supra (sugar modifications). Workers have attached certain tether functionalities to the 3-position of 3-deaza-adenine. *The Chemistry of Heterocyclic Compounds*, A. Weissberger, Ed., Imidazole and Derivatives, Part 1, Interscience, N.Y. (1953). However, there has been no investigation into the synthesis of 3-C substituted deazaguanine. The present invention is the first to set forth substitutions at the 3-C position of 3-deazaguanines and 3-deazapurine derivatives.

The bulkiest 3-C deazapurine substituent induces an unnatural 3'-endo/high-anti (−sc) conformation of the nucleoside. This preference for the anti-conformation may make the 2'-deoxy 3-deazapurines of the invention enhanced substrates for viral kineses. Further, substitutions at the C-3 aromatic carbon of the 3-deazapurine ring system are of interest because this influences the heterocycle's range of rotation about the glycosidic bond, Saenger, "Principles of Nucleic Acid Structure," Cantor, C. R., Ed., Springer-Verlag, New York, 1983, potentially modifying biological activity, Saran, et al., *Int. J. Quantum Chem.* 1984 25, 743; Miles, et al., *H.J. Theor. Biol.* 1977, 67, 499. Further, lipophilic substituents at this position could change the transport efficiency of heterocyclic bases, heterocyclic base analogs, nucleosides, nucleoside analogs, nucleotides, nucleotide analogs, and oligonucleotides compositions.

SUMMARY OF THE INVENTION

This invention presents novel compounds based on the 3-deazapurine ring system that have utility as intermediates for oligonucleotide compositions. This invention also provides novel synthetic methods for the preparation of these compounds employing a mild alkylation procedure on an imidazole precursor to this ring system. In particular, this invention provides nucleosides, nucleoside analogs, nucleotides, nucleotide analogs, heterocyclic bases, and heterocyclic base analogs. These heterocyclic compounds are adapted for placement of the reactive, RNA cleaving moiety or other reactive moiety into the minor groove site of the hybrid structure formed from the RNA and the composition through careful selection of the attachment of the RNA cleaving moieties.

The compounds of the invention possess unique steric properties that result in modified biological activity and better cellular transport properties for oligonucleotide compositions. These attributes make these compositions useful oligonucleotide intermediates.

In one aspect of the invention, the compounds have the formula:

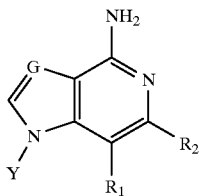

wherein G is C or N; $R_1$ is $NH_2$, alkyl, substituted alkyl, alkenyl, substituted alkenyl, aralkyl, amino, alkylamino, aralkylamino, substituted alkylamino, heterocycloalkyl, heterocycloalkylamino, aminoalkylamino, hetrocycloalkylamino, polyalkylamino, or an RNA cleaving moiety; $R_2$ is alkyl, substituted alkyl, alkenyl, substituted alkenyl, aralkyl, amino, alkylamino, aralkylamino, substituted alkylamino, heterocycloalkyl, heterocycloalkylamino, aminoalkylamino, hetrocycloalkylamino, polyalkylamino, or an RNA cleaving moiety; and Y is H, a nitrogen protecting group, or a sugar moiety.

In certain preferred embodiments, Y is ribose. In a more preferred embodiment, Y is deoxyribose. In another preferred embodiment, Y is a sugar analog, preferably the deoxyribose type.

In certain preferred embodiments, $R_1$ is alkyl having up to about 12 carbon atoms. In another preferred embodiment, $R_1$ is alkenyl having up to about 12 carbon atoms. In still another preferred embodiment, $R_1$ is aralkyl having from about 6 to about 30 carbon atoms.

In other preferred embodiments, Y is ribose or deoxyribose and $R_1$ is alkyl having up to about 12 carbon atoms. In another preferred embodiment, Y is ribose or deoxyribose and $R_1$ is alkenyl having up to about 12 carbon atoms. In yet another preferred embodiment, Y is ribose or deoxyribose and $R_1$ is aralkyl having from about 6 to about 30 carbon atoms.

In certain other preferred embodiments, G is N, $R_1$ is alkyl, $R_2$ is amino, and Y is ribose or deoxyribose. In another preferred embodiment, G is N, $R_1$ is alkenyl, $R_2$ is amino, and Y is ribose or deoxyribose. In other preferred embodiments, G is N, $R_1$ is aralkyl, $R_2$ is amino, and Y is ribose or deoxyribose. In other preferred embodiments, G is N; $R_1$ is 1-methyloctane, 1-propene, phenylmethyl, or napthylethyl; $R_2$ is amino; and Y is ribose or deoxyribose.

In certain preferred embodiments, the RNA cleaving moiety comprises a portion reactive with said RNA. In another preferred embodiment, the RNA cleaving moiety further comprises a tether portion for attaching the reactive portion to the balance of the composition.

Numerous amine protecting groups are known in the art, and can be used, including the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38). For example, it is known that the Boc group can protect an amine group from base and from reducing conditions but that it can be removed with acid.

The invention further provides compositions comprising a sugar and base moiety as discussed above, with the 3' position of the sugar moiety derivatized with an activated phosphate group.

In another aspect of this invention, mixed sequence oligonucleotides incorporating at least one compound as set forth above are presented.

In another aspect of the invention, the compounds have the formula:

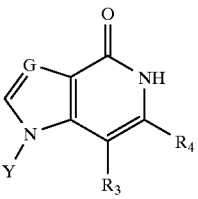

wherein G is C or N; $R_3$ is H, $NH_2$, alkyl, substituted alkyl, alkenyl, substituted alkenyl, aralkyl, amino, alkylamino, aralkylamino, substituted alkylamino, heterocycloalkyl, heterocycloalkylamino, aminoalkylamino, hetrocycloalkylamino, polyalkylamino, or an RNA cleaving moiety; $R_4$ is $NH_2$, alkyl, substituted alkyl, alkenyl, substituted alkenyl, aralkyl, amino, alkylamino, aralkylamino, substituted alkylamino, heterocycloalkyl, heterocycloalkylamino, aminoalkylamino, hetrocycloalkylamino, polyalkylamino, or an RNA cleaving moiety; and Y is H, a nitrogen protecting group, or a sugar moiety; provided that when $R_3$ is H, $R_4$ is not $NH_2$.

In certain preferred embodiments, Y is ribose. In a more preferred embodiment, Y is deoxyribose. In another preferred embodiment, Y is a sugar analog, preferably the deoxyribose type.

In certain preferred embodiments, $R_3$ is alkyl having up to about 12 carbon atoms. In another preferred embodiment, $R_3$ is alkenyl having up to about 12 carbon atoms.

In still another preferred embodiment, $R_3$ is aralkyl having from about 6 to about 30 carbon atoms.

In other preferred embodiments, Y is ribose or deoxyribose and $R_3$ is alkyl having up to about 12 carbon atoms. In another preferred embodiment, Y is ribose or deoxyribose and $R_3$ is alkenyl having up to about 12 carbon atoms. In yet another preferred embodiment, Y is ribose or deoxyribose and $R_3$ is aralkyl having from about 6 to about 30 carbon atoms.

In certain other preferred embodiments, G is N, $R_3$ is alkyl, $R_4$ is $NH_2$, and Y is ribose or deoxyribose. In another preferred embodiment, G is N, $R_3$ is alkenyl, $R_4$ is $NH_2$, and Y is ribose or deoxyribose. In other preferred embodiments, G is N, $R_3$ is aralkyl, $R_4$ is $NH_2$, and Y is ribose or deoxyribose.

In certain preferred embodiments, the RNA cleaving moiety comprises a portion reactive with said RNA. In another preferred embodiment, the RNA cleaving moiety further comprises a tether portion for attaching the reactive portion to the balance of the composition.

Numerous amine protecting groups are known in the art, and can be used, including the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38). For example, it is known that the Boc group can protect an amine group from base and from reducing conditions but that it can be removed with acid.

The invention further provides compositions comprising a sugar and base moiety as discussed above, with the 3' position of the sugar moiety derivatized with an activated phosphate group.

In another aspect of this invention, mixed sequence oligonucleotides incorporating at least one compound as set forth above are presented.

In another aspect of the invention, novel methods for synthesizing the compounds of the invention are provided. The synthesis of the 3-deazaguanine ring system has been most widely achieved via the base-catalyzed cyclization of a 5(4)-cyanomethyl-imidazole-4(5)-carboxamide. Cook, et al., *J. Am. Chem. Soc.* 1975, 97, 2916; Cook, et al., *R.K. J. Med. Chem.* 1978, 21, 1212, the disclosures of which are incorporated herein by reference in their entirety. Both the 2'-deoxy- and the 3-deazaguanosines have also been synthesized using a synthetic scheme that relies on this novel cyclization.

Generally, the compounds of the invention may be synthesized by employing a mild alkylation on the methylene carbon of an imidazole precursor to the 3-deazapurine ring system. The starting material may be a 5-cyano-methyl-imidazole carboxylate, which can be synthesized according to a known procedure. *Journal of Medicinal Chemistry*, Vol. 27 p. 1389 (1984). For nucleoside synthesis, a sugar moiety is attached to the 1-position of the imidazole ring of the starting material before the alkylation step. Methods of attaching a sugar moity to the imidazole ring are well known to those skilled in the art.

For base synthesis, the ester functionality of the starting material, 5 cyanoimidazole carboxylate, is protected with an ester protecting group before the alkylation step. Any ester protecting groups and methods of attaching ester protecting groups known in the art may be used.

Generally, reactive functionalities emanating from the 3-position of the 3-deazapurine ring can be obtained by a multi-step synthesis under the following reaction conditions. The methylene moiety of the staring material is alkylated with halogenated reactive functionalities, such as an alkyl, alkenyl, or aryl halide.

The alkylated carboxylates are converted to the corresponding carboxamides by ammonolysis at elevated temperature. The alkylated carboxamides are subsequently cyclized using one of several available procedures. Cook, et al., *J. Am. Chem. Soc.* 1975, 97, 2916; Cook, et al., *R.K. J. Med. Chem.* 1978, 21, 1212. For example, cyclized products can be obtained using a two-step procedure employing liquid and methanolic ammonia. The protecting groups are removed from the imidazole intermediate with hydrochloric acid.

The corresponding nucleotides of the invention can be prepared by protecting the 5' position of the sugar moiety of a nucleosidic unit and derivatizing the 3' position with an appropriate phosphoramidite or other activated phosphate. These are inserted into oligonucleotides as 5'-DMT-3'-cyanoethyl phosphoramidites through routine solid state synthetic techniques.

Oligonucleotide or oligonucleotide analogs incorporating at least one of the novel compounds of the invention may be synthesized and are within the ambit of this invention. Oligonucleotides or oligonucleotide analogs incorporating the novel compounds of the invention may be synthesized, conveniently through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide of reasonable length which may be desired. See, e.g., Caruthers, *Oligonucleotides, Antisense Inhibitors of Gene Expression.*, pp. 7–24, J. S. Cohen, ed. (CRC Press, Inc. Boca Raton, Fla., 1989); *J. Am. Chem. Society*, 1990, 112, 1253–1255; Beaucage et al., *Tetrahedron Letters*, 1981, 22, 1859–1862.

The sugar moiety of the nucleosidic units incorporated onto the oligonucleotide compositions is preferably the deoxyribose type. The groups linking the bases together may be the usual sugar phosphate nucleic acid backbone, but may also be modified as a phosphorothioate, methylphosphonate, or phosphate alkylated moiety to further enhance the sugar modified oligonucleotide properties, along with removal of a 5'-methylene group and/or carbocyclic sugar. Sugar modifications are disclosed as set forth in Ser. No. 07/845,634, the disclosure of which are incorporated herein by reference in order to disclose more fully such modifications.

DETAILED DESCRIPTION OF THE INVENTION

This invention presents novel heterocyclic compounds based on the 3-deazapurine core that may be used intermediates for oligonucleotide compositions. In particular, this invention provides nucleosides, nucleoside analogs, nucleotides, nucleotide analogs, heterocyclic bases, and heterocyclic base analogs. The compounds of the invention possess unique steric properties that result in modified biological activity and better cellular transport properties. These attributes make these compositions useful intermediates for oligonucleotide compositions.

The compounds of the invention may have at least one RNA cleaving moiety or other moiety capable of interacting with an RNA appended thereto, which are adapted for placement of the reactive RNA cleaving moiety or other reactive moiety into the minor groove site of the hybrid structure formed from the RNA and the composition through careful selection of the sites of attachment of the RNA cleaving moieties. Incorporation of these novel compounds into oligonucleotides compositions improves these compositions' pharmacokinetic and pharmacodynamic properties, the compositions' resistance to nucleases, improves the compositions' binding capabilities without any concomitant interference with the Watson-Crick binding, and enhances the compositions' penetration into cells.

The functionalized sites on the base units, which in turn may be incorporated into modified oligonucleotides, is critical in the design of compositions for sequence-specific destruction or modulation of targeted RNA. The functionality must not interfere with Watson-Crick base pair hydrogen bonding rules as this is the sequence-specific recognition/binding factor essential for selection of the desired RNA to be disrupted.

It has now been found that certain positions on the nucleosides of double stranded nucleic acids are exposed in the minor groove and may be substituted without affecting Watson-Crick base-pairing or duplex stability. Reactive or non-reactive functionalities placed in these positions in accordance with this invention can best initiate cleavage and destruction of targeted RNA or interfere with its activity. The sites of functionality in the heterocyclic compounds of the invention are novel, and have been preferably designed such that the functionalities will reside in or on the minor groove formed by the heteroduplex between modified oligonucleotides and targeted RNA.

The present invention also provides novel methods for the synthesis of the compounds of the invention employing a mild alkylation procedure on an imidazole precursor to the 3-deazapurine ring system.

The compounds possessing the required functionality in the heterocyclic base portion may be used to prepare desired oligonucleotides and oligonucleotide analogs. These oligonucleotide and oligonucleotide analogs are also within the ambit of this invention. Oligonucleotides and oligonucleotide analogs incorporating the novel compounds of the invention are believed to increase the oligonucleotide compositions' nuclease resistance, and thus, facilitate antisense therapeutic, diagnostic use, or research reagent use of these antisense agents.

In the context of this invention, a "nucleoside" is a nitrogenous heterocyclic base linked to a pentose equivalent, either a ribose, deoxy ribose, or derivative or analog thereof. The term "nucleotide" means a phosphoric acid ester of a nucleoside comprising a nitrogenous heterocyclic base, a pentose equivalent, and one or more phosphate or other backbone forming groups; it is the monomeric unit of an oligonucleotide. The term "oligonucleotide" refers to a plurality of joined nucleotide units formed in a specific sequence from naturally occurring heterocyclic bases and pentofuranosyl equivalent groups joined through phosphodiester or other backbone forming groups. Nucleotide units may be nucleic acid bases such as guanine, adenine, cytosine, thymine, or derivatives thereof. The pentose equivalent may be deoxyribose, ribose, or groups that substitute therefore. This term refers to both naturally occurring and synthetic species formed or derived from naturally occurring subunits. The terms "antisense agents" and "oligonucleotide compositions" as used in the context of this invention encompass oligonucleotides and oligonucleotide analogs. In the context of this invention, "activated phosphate group" means phosphorothioates, methyl phosphonates, phosphoramidites, and phosphorotriesters (phosphate methylated DNA) and any other groups known to those skilled in the art.

"Modified base," "base analog," "modified nucleoside," "nucleotide analog," or "modified nucleotide," in the context of this invention refer to moieties that function similarly to their naturally occurring counterparts but have been functionalized to change their properties.

"Sugar moiety" as used in the context of this invention refers to naturally occurring sugars, such as ribose or deoxyribose, and sugars and non-sugar analogs that have been functionalized to change their properties.

"Oligonucleotide analogs" or "modified oligonucleotides" as used in connection with this invention, refer to compositions that function similarly to natural oligonucleotides but that have non-naturally occurring portions. Oligonucleotide analogs or modified oligonucleotides may have altered sugar moieties, altered bases, both altered sugars and bases or altered inter-sugar linkages, for example phosphorothioates and other sulfur containing species which are known for use in the art.

In the context of the invention, "improved pharmacodynamic property" means improved oligonucleotide uptake, enhanced oligonucleotide resistance to degradation, and/or strengthened sequence-specific hybridization with RNA. "Improved pharmacokinetic property" means improved oligonucleotide uptake, distribution, metabolism or excretion.

In one aspect of the invention, the compounds have the formula:

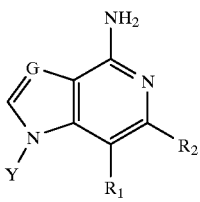

wherein G is C or N; $R_1$ is $NH_2$, alkyl, substituted alkyl, alkenyl, substituted alkenyl, aralkyl, amino, alkylamino, aralkylamino, substituted alkylamino, heterocycloalkyl, heterocycloalkylamino, aminoalkylamino, hetrocycloalkylamino, polyalkylamino, or an RNA cleaving moiety; $R_2$ is alkyl, substituted alkyl, alkenyl, substituted alkenyl, aralkyl, amino, alkylamino, aralkylamino, substituted alkylamino, heterocycloalkyl, heterocycloalkylamino, aminoalkylamino, hetrocycloalkylamino, polyalkylamino, or an RNA cleaving moiety; and Y is H, a nitrogen protecting group, or a sugar moiety.

In certain preferred embodiments, Y is ribose or deoxyribose. In a more preferred embodiment, Y is deoxyribose. In another preferred embodiment, Y is a sugar analog, preferably the deoxyribose type. Sugar analogs with substituents at the 3' or 5' of deoxyribose, or at the 2', 3', or 5' of ribose are contemplated. Suitable substituents on the sugar moiety include, but are not limited to, O, H, lower alkyl, substituted lower alkyl, aralkyl, heteroaralkyl, heterocycloalkyl, aminoalkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH=CH_2$, $OCH_2CCH$, OCCH, or an RNA cleaving moiety.

Generally, substituted sugars may be synthesized according to the methods disclosed in U.S. Ser. No. 07/854,634, the disclosure of which are incorporated herein by reference to disclose more fully such modifications.

For example, a substituted sugar as, methyl 3-O-(t-butyldiphenylsilyl)-2,5-dideoxy-5-C-formyl-α/β-D-erythro-pentofuranoside, can be prepared by modifying 2-deoxy-D-ribose to methyl 2-deoxy-α/β-D-erythro-pentofuranoside (prepared according to the method of M. S. Motawai and E. B. Pedersen, Liebigs Ann. Chem. 1990, 599–602), which on selective tosylation followed by 3-O-silylation gave methyl 3-O-(t-butyldimethylsilyl)-2-deoxy-5-O-tosyl-α/β-D-erythro-pentofuranoside.

In certain other preferred embodiments, $R_1$ is alkyl having up to about 12 carbon atoms. In another preferred embodiment, $R_1$ is alkenyl having up to about 12 carbon atoms. In still another preferred embodiment, $R_1$ is aralkyl having from about 6 to about 30 carbon atoms. In another preferred embodiment, $R_1$ is 1-methyloctane. In a more preferred embodiment, $R_1$ is 1-propene. In still a more preferred embodiment, $R_1$ is phenylmethyl. In yet a more preferred embodiment, $R_1$ is napthylethyl.

In other preferred embodiments, Y is ribose or deoxyribose and $R_1$ is alkyl having up to about 12 carbon atoms. In another preferred embodiment, Y is ribose or deoxyribose and $R_1$ is alkenyl having up to about 12 carbon atoms. In yet another preferred embodiment, Y is ribose or deoxyribose and $R_1$ is aralkyl having from about 6 to about 30 carbon atoms.

In certain other preferred embodiments, G is N, $R_1$ is alkyl, $R_2$ is amino, and Y is ribose or deoxyribose. In another preferred embodiment, G is N, $R_1$ is alkenyl, $R_2$ is amino, and Y is ribose or deoxyribose. In other preferred embodiments, G is N, $R_1$ is aralkyl, $R_2$ is amino, and Y is ribose or deoxyribose. In other preferred embodiments, G is N; $R_1$ is 1-methyloctane, 1-propene, phenylmethyl, or napthylethyl; $R_2$ is amino; and Y is ribose or deoxyribose.

$R_1$ and/or $R_2$ may be any of the following alkyl, alkenyl, aryl, amino, or cyclic groups. Alkyl groups of the invention include, but are not limited to, $C_1$–$C_{12}$ straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methyl-pentyl, 3-methylpentyl, 2-ethylhexyl, 2-propylpentyl. Alkenyl groups include but are not limited to unsaturated moieties derived from the above alkyl groups including but not limited to vinyl, allyl, crotyl, propargyl. Aryl groups include but are not limited to phenyl, tolyl, benzyl, naphthyl, anthracly, phenanthryl, and xylyl. Suitable heterocyclic groups include but are not limited to imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Amines are also meant to include polyalkylamino compounds and aminoalkylamines such as aminopropylamine and further heterocycloalkylamines such as imidazol-1, 2 or 4-yl-propylamine. Substituent groups for the above include but are not limited to other alkyl, haloalkyl, alkenyl, alkoxy, thioalkoxy, haloalkoxy and aryl groups as well as halogen, hydroxyl, amino, azido, carboxy, cyano, nitro, mercapto, sulfides, sulfones and sulfoxides. Other suitable substituent groups also include rhodamines, coumarins, acridones, pyrenes, stilbenes, oxazolopryidocarbazoles, anthraquinones, phenanthridines, phenazines, azidobenzenes, psoralens, porphyrins and cholesterols. Pendant groups that do not possess reactive functionality, do not initiate chemical reactions, but enhance the oligonucleotide compositions' pharmacodynamic and pharmacokinetic properties may also be used without departing from the spirit of the invention. Such groups include, but are not limited to, alkyl chains, polyamines, ethylene glycols, polyamides, aminoalkyl chains, amphipathic moieties, points for reporter group attachment, and intercalators attached to any of the preferred sites for attachment.

In other preferred embodiments, the RNA cleaving moiety comprises a portion reactive with said RNA. It is believed desirable in accordance with certain preferred embodiments, to attach the RNA cleaving portion to one of the nucleosides forming the subunits of the oligonucleotide compositions' targeting portion.

In another preferred embodiment, the RNA cleaving moiety further comprises a tether portion for attaching the reactive portion to the balance of the composition. It is not necessary to tether more than one, or perhaps two RNA cleaving functionalities to oligonucleotide compositions in accordance with this invention in order to provide the benefits of the invention. Thus, an RNA cleaving moiety will preferably be tethered to a relatively small proportion of the subunits, generally only one or two, comprising the oligonucleotide compositions, which is the targeting portion of the compositions of the invention. In other embodiments, of the invention, however, all of the nucleotides in an oligonucleotide can be modified to include one or more RNA cleaving moiety groups.

The half life of the perfectly formed duplex will be greatly effected by the positioning of the tethered functional group. Inappropriate positioning of functional groups, such as placement on the Watson/Crick base pair sites, would preclude duplex formation. Other attachment sites may allow sequence-specific binding but may be of such low stability that the reactive functionality will not have sufficient time to initiate RNA disruption.

It is believed that attaching RNA cleaving moieties in accordance with the foregoing considerations will permit those moieties to lie in the minor groove of the hybrid formed from the composition of the present invention and the messenger RNA for which modulation is desired. It is possible that other positions for attachment of the RNA cleaving moieties having a similar effect may be found, especially when further modifications of the purine structure is undertaken as may be done by persons of ordinary skill in the art without deviating from the spirit of the present invention. Once again, it is to be understood that preferably one, or at most a few RNA cleaving moieties are generally to be employed. Thus, artisans in the field will have great latitude in selecting means of attachment of the RNA cleaving moieties, the pharmacodynamic improving group or the pharmacokinetic improving group in accordance with this invention.

The RNA cleaving moieties of the compositions of the present invention are designed in such a fashion that they can be effective in performing their proximate task, leading to the desired modulation of RNA activity. RNA cleaving moieties may include heteroatomic substitutions; these heteroatomic substituents include, but are not limited to, amides and polyamides, and heterocyclics, especially imidazoles and other nitrogen heterocycles.

Generally, protecting groups are known per se as chemical functional groups that can be selectively appended to and removed from functionalities, such as amine groups. These groups are present in a chemical compound to render such functionality inert to chemical reaction conditions to which the compound is exposed. See, e.g., Greene and Wuts, Protective Groups in Organic Synthesis, 2d edition, John Wiley & Sons, New York, 1991. Numerous amine protecting groups are known in the art, including, but not limited to, the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38). For example, it is known that the Boc group can protect an amine group from base and from reducing conditions but that it can be removed with acid. Other nitrogen protecting groups will be apparent to those skilled in the art and may be used without detracting from the spirit of the invention.

Another aspect of the invention presents compounds having the formula:

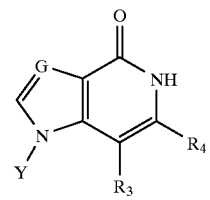

wherein G is C or N; $R_3$ is H, $NH_2$, alkyl, substituted alkyl, alkenyl, substituted alkenyl, aralkyl, amino, alkylamino, aralkylamino, substituted alkylamino, heterocycloalkyl, heterocycloalkylamino, aminoalkylamino, hetrocycloalkylamino, polyalkylamino, or an RNA cleaving moiety; $R_4$ is $NH_2$, alkyl, substituted alkyl, alkenyl, substituted alkenyl, aralkyl, amino, amino alkylamino, aralkylamino, substituted alkylamino, heterocycloalkyl, heterocycloalkylamino, aminoalkylamino, hetrocycloalkylamino, polyalkylamino, or an RNA cleaving moiety; and Y is H, a nitrogen protecting group, or a sugar moiety; provided that when $R_3$ is H, $R_4$ is not $NH_2$.

In certain preferred embodiments, Y is ribose or deoxyribose. In a more preferred embodiment, Y is deoxyribose. In another preferred embodiment, Y is a sugar analog, preferably the deoxyribose type. Sugar analogs with substituents at the 3' or 5' of deoxyribose, or at the 2', 3', or 5' of ribose are contemplated. Suitable substituents on the sugar moiety include, but are not limited to, O, H, lower alkyl, substituted lower alkyl, aralkyl, heteroaralkyl, heterocycloalkyl, aminoalkylamino, heterocycloalkyl, polyalkylamino, substituted silyl, F, Cl, Br, CN, $CF_3$, $OCF_3$, OCN, O-alkyl, S-alkyl, $SOMe$, $SO_2Me$, $ONO_2$, $NO_2$, $N_3$, $NH_2$, NH-alkyl, $OCH_2CH=CH_2$, $OCH=CH_2$, $OCH_2CCH$, OCCH, or an RNA cleaving moiety. The discussion of sugar moieties set forth above in connection with the other compounds of the invention is fully applicable here.

In certain preferred embodiments, $R_3$ is alkyl having up to about 12 carbon atoms. In another preferred embodiment, $R_3$ is alkenyl having up to about 12 carbon atoms. In still another preferred embodiment, $R_1$ is aralkyl having from about 6 to about 30 carbon atoms. In a more preferred embodiment, $R_3$ is 1-methyloctane. In a more preferred embodiment, $R_3$ is 1-propene. In still a more preferred embodiment, $R_3$ is phenylmethyl. In yet a more preferred embodiment, $R_3$ is napthylethyl.

In other preferred embodiments, Y is ribose or deoxyribose and $R_3$ is alkyl having up to about 12 carbon atoms. In another preferred embodiment, Y is ribose or deoxyribose and $R_3$ is alkenyl having up to about 12 carbon atoms. In yet another preferred embodiment, Y is ribose or deoxyribose and $R_3$ is aralkyl having from about 6 to about 30 carbon atoms.

In certain other preferred embodiments, G is N, $R_3$ is alkyl, $R_4$ is $NH_2$, and Y is ribose or deoxyribose. In another preferred embodiment, G is N, $R_3$ is alkenyl, $R_4$ is $NH_2$, and Y is ribose or deoxyribose. In other preferred embodiments, G is N, $R_3$ is aralkyl, $R_4$ is $NH_2$, and Y is ribose or deoxyribose. In other preferred embodiments, G is N; $R_3$ is 1-methyloctane, 1-propene, phenylmethyl, or napthylethyl; $R_4$ is amino; and Y is ribose or deoxyribose.

$R_3$ and $R_4$ may be any of the alkyl, alkenyl, aryl, amino, or cyclic groups as set forth above.

In other preferred embodiments, the RNA cleaving moiety and nitrogen protecting groups may be as set forth above in connection with the previously discussed compounds. The discussion set forth above is fully applicable here.

Generally, the bases of the invention may be synthesized by starting with a 5-cyanomethyl imidazole carboxylate, protecting the ester with an ester protecting group, treating the compound with sodium hydride, followed by electrophilic substitution with an alkyl, alkenyl, or aryl halide, preferably bromine. The carboxylates are converted to the corresponding carboxamides by treatment with methanolic ammonia at elevated temperature. The alkylated products are subsequently cyclized. Cook, et al., *J. Am. Chem. Soc.* 1975, 97, 2916; Cook, et al., *R.K. J. Med. Chem.* 1978, 21, 1212; Revankar, supra.

The following discussion provides an illustrative example of a possible synthetic route. The bases of the invention may be synthesized by protecting the methyl 5(4)-cyanomethyl-imidazole-4(5)-carboxylate's imidazole ring nitrogens with a protecting group such as a tetrahydropyranyl group. A reaction with 2,3-dihydropyran in the presence of tosic acid yields the 5 and 7 tetrahydropyranyl positional isomers of 4-cyanomethyl-imidazole-5-carboxylates in roughly a 2:1 ratio. These isomers are separated in order to isolate the isomer with a tetrahydropyranyl protecting group in a position removed from the proposed site of alkylation. Cook et al., *J. Med. Chem.*, 1978, 21, 1212.

The 7 tetrahydropyranyl positional isomer is then alkylated by adding a dilute solution of the alkylating electrophile in acetonitrile to the reaction mixture, the reaction mixture is stirred under an inert atmosphere for periods of 3–18 hours. The reaction media and products are isolated by flash-column chromatography using silica gel. In each case, the products are approximately 1:1 mixtures of isomers, as determined by an integration of the signals for the H-2 protons in the $^1$H-NMR. The alkylated product mixtures were subsequently treated with methanolic ammonia and heated at 75° C. in a sealed vessel to yield the cyclized products. When the ammonolysis was conducted at 100° C., there was extensive decomposition and no products could be isolated. The mixtures were evaporated under reduced pressure to afford light colored solids which decomposed rapidly when exposed to air and moisture. The crude reaction products were thoroughly rid of all ammonia and treated with 1 N HCl in methanol for several hours to remove the tetrahydropyranyl protecting groups, which yielded the 7-alkyl (aryl)-6-amino-1,5-dihydroimidazo [4,5-c]pyridin-4-one products as stable hydrochloride salts. Hartman, et al., *J. Labelled Compd. Radiopharm.*, 1985, 23, 35. The hydrochloride salts gave satisfactory C,H,N analyses and $^1$H-NMR spectra after months of storage, attesting to their long-term stability. The following reaction scheme illustrates this synthesis.

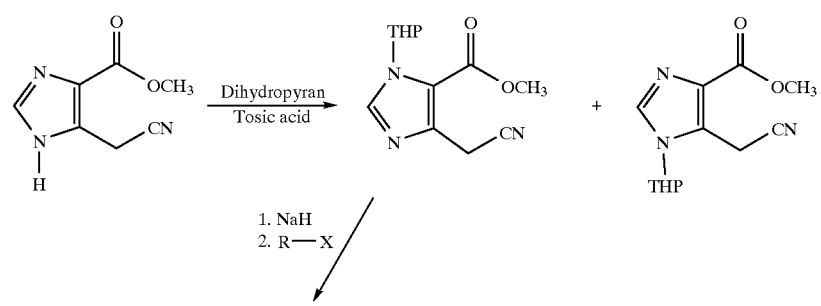

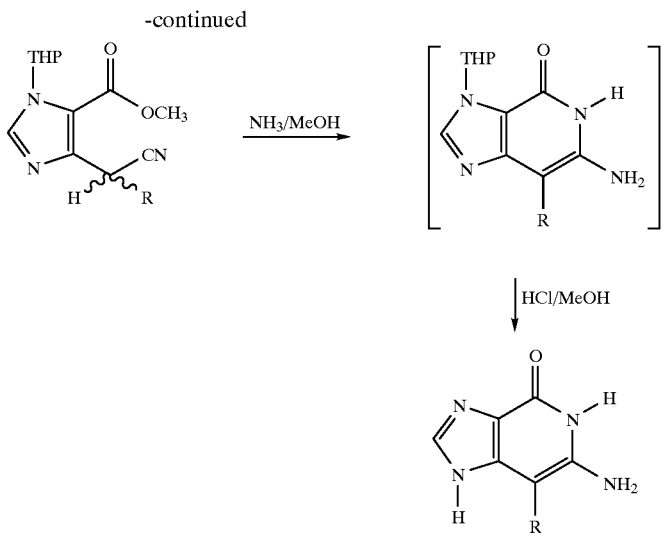

Compounds of the invention having a sugar moiety at the 1-position of the imidazole ring invention may be synthesized using a procedure similar to that used for the previously discussed bases of the invention. Generally, reactive functionalities emanating from the 3-position of a 2'-deoxy-3-deazapurine can be obtained by a multi-step synthesis starting with the alkylation of the methylene moiety of a cyanomethyl imidazole derivative with various electrophiles, such as halogenated reactive functionalities. The alkylated product is ammonylated to yield the carboxamide. The carboxamide of methyl-5-(cyanomethyl)-1-(2'deoxy-3,5-di-O-p-toluyl-β-D-erythro-pentofuranosyl) imidazole-4-carboxylate may be obtained from the ammonolysis of the methyl 5-cyanomethyl-imidazole-4-carboxylates, and 5-cynanomethyl-1-(2-deoxy-3,5-di-O-p-toluoylp-β-D-erythro-pentofuranosyl)-imidazole-4-carboxylate. Cyclized products may be obtained using a two-step procedure employing liquid and then methanolic ammonia. The alkylated imidazoles are treated with methanolic ammonia to remove the toluoyl groups from the sugar moiety. These may be inserted into oligonucleotides as 5'-DMT-3'-cyanoethyl phosphoramidites through routine solid state synthetic techniques.

The starting imidazole material, 5-cyano (substituted)-methyl-1-(2'-deoxy-3,5-di-O-p-toluoyl-β-D-erythro-pentofuranosyl)imidazole-4-carboxylate, for the above discussed reaction, can be synthesized according to a known procedure. Journal of Medicinal Chemistry, Vol. 27 p. 1389 (1984). The synthetic intermediate methyl-5-(cyanomethyl)-1-(2'deoxy-3,5-di-O-p-toluyl-β-D-erythro-pentofuranosyl) imidazole-4-carboxylate was obtained from the sodium salt glycosylation of methyl 5(4)-cyanomethyl-imidazole-4(5) carboxylate with 1-chloro-2-deoxy-3,5-di-O-p-toluoyl-a-D-erythro-pentofuranose (chlorosugar) in acetonitrile. Positional isomers corresponding to methyl 5-cynanomethyl-1-(2-deoxy-3,5-di-O-p-toluoylp-β-D-erythro-pentofuranosyl)-imidazole-4-carboxylate and methyl 4-cyanomethyl-1-(2-deoxy- 3,5-di-O-p-toluoyl-b-D-erythro-pentofuranosyl)-imidazole 5-carboxylate were obtained in 1:1.5 ratios and in good overall yields. The most favorable ratio of positional isomers was obtained when the chloro-sugar used in the condensation was free of acidic contaminants and anhydrous conditions were maintained during the course of the reaction. Revankar, supra. Other synthetic methods will be apparent to those skilled in the art.

The nucleosides may be synthesized under the following reaction conditions. The 5-cynanomethyl-1-(2-deoxy-3,5-di-O-p-toluoylp-β-D-erythro-pentofuranosyl)imidazole-4-carboxylate was equilibrated with an excess of sodium hydride at room temperature in acetonitrile. A dilute solution of the alkylating agent in acetonitrile was introduced into the reaction mixture and the reaction mixture stirred under an inert atmosphere for a period of 3–18 hours. The reaction media and products are then isolated by flash-column chromatography. This procedure yields mixtures of diastereomeric products. For example, in the case of the methyl 5-(benzyl[cyano]methyl)imidazole-4-carboxylate or the methyl 5-(cyano[2-(1-naphthyl)ethyl]methyl)imidazole-4-carboxylate 2'-deoxynucleosides, these mixtures were resolved according to the procedures specified in Cook, J. Med. Chem., supra.

For example, in the case of the methyl 5-(benzyl [cyano] methyl)imidazole-4-carboxylate or the methyl 5-(cyano [2-(1-naphthyl)ethyl]methyl)imidazole-4-carboxylate 2'-deoxynucleosides, these mixtures were resolved and the diastereomers characterized individually by $^1$H-NMR. In these cases, each isomer exhibited a methene proton resonance as a doublet of doublets at δ,4.8 to 5.5 ppm, indicative of a tertiary proton, Pretsch, supra, as part of an $AM_2$ system. In addition, these compounds exhibited nitrile absorption bands at 2220 to 2240 $cm^{-1}$ in their infrared spectra.

The alkylation products, methyl 5-(cyano[alkyl]methyl)-1-(2-deoxy-3,5di-O-p-toluoyl-O-D-erythro-pentofuranosyl) imidazole-4-carboxylate nucleosides are heated in liquid ammonia at 90° C. for 18–20 hours in a stainless steel bomb to yield the corresponding deprotected carboxamides. Further heating of the carboxamides with methanolic ammonia at 95° C. yields the desired nucleoside products, 2'-deoxy-3-alkyl(aryl)-3-deazapurines. This two step procedure resulted in better yields of the cyclized products than obtained by prolonged heating of the methyl 5-cyanomethyl-imidazole-4-carboxylates in liquid ammonia. Cook, J. Am. Chem. Society, supra. The following reaction scheme illustrates the synthesis of the nucleosides of the invention.

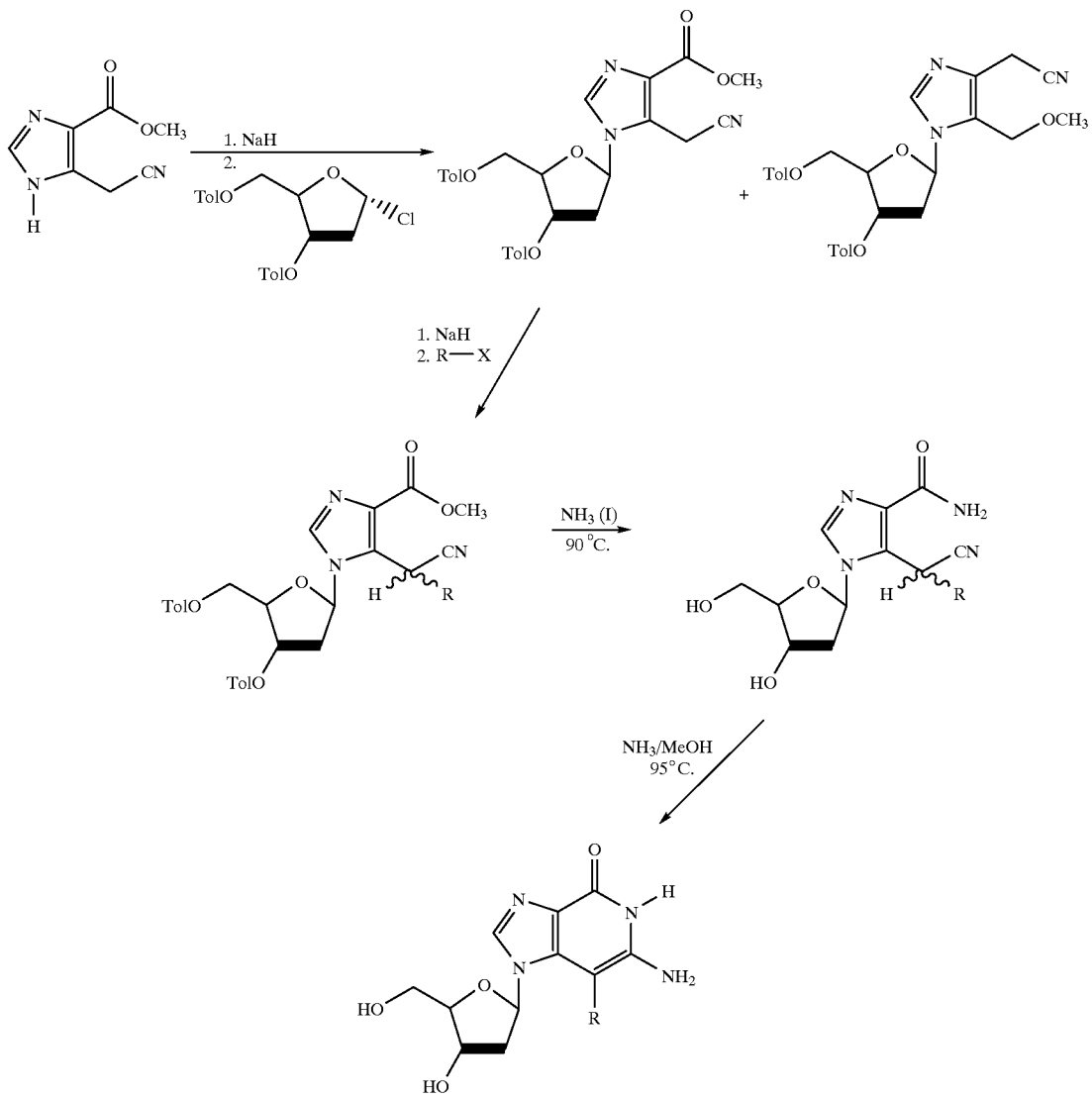

The electrophiles suitable for practicing the invention include, but are not limited to, alkyl, alkenyl, aryl, amino, cyclic, or heterocyclic compounds having a group. The suitable leaving groups include, but are not limited to, chloride, flouride, iodine, and bromine, with bromine preferred.

Any ester protecting groups known to those skilled in the art may be used; tetrahydropyranyl is an example of such a group. However, various ester protecting groups are known and may be used without detracting from the spirit of the invention. See Greene and Wuts, supra.

Methods of synthesizing compounds where the 3 position of the imidazole ring system is carbon rather than nitrogen will be apparent to those skilled in the art and may be used without detracting from the spirit of the invention. See Revankar, supra.

Methods of attaching sugar moieties to the imidazole ring are well known in the art. See Revankar, supra.

In preparing certain of the compounds of the invention fugitive masking groups may be used. Such masking groups allow for ease of synthesis of the compounds. The masking groups are subsequently converted to the desired functionality. Such conversion preferably occurs during a standard deblocking step for a later reaction. As an example of use of this procedure is the use of phthalimide group for the introduction of an amino functionality. Alkyl phthalimides are attached at the proper position in a compound of interest, as for example a nucleoside, via a suitable intermediate such as an N-(haloalkyl)phthalimide. Upon completion of the synthesis of the compound of interest it is then used as a structural nucleotide for oligonucleotide synthesis utilizing standard oligonucleotide synthetic techniques on a nucleotide synthesizer. After the desired oligonucleotide or oligonucleotide analog is completed, it is cleaved from the synthesizer support and in doing so the cleaving reagent also converts the alkylphthalimide to the desired alkylamine. The above procedure can be expanded to attach longer chain polyamino functionalities to the oligonucleotides or oligonucleotide analogs of the invention. Nucleotides, nucleotide analogs, oligonucleotide analogs, or oligonucleotides having a first alkylamino functionality are treated with a further N-(haloalkyl) phthalimide. The extended functionality is then treated to yield the terminal amine group. This can be repeated to further extend the polyamino functionality as desired. Alternately, the extended polyamino functionality is first synthesized and reacted with the first alkylamino functionality to form the polyamino functionality.

If any of the reactions yield a reaction slurry from which the product must be recovered this can be done according to nay methods known in the art. Methods of recovering the sample include any filtration or separation techniques known in the art. Such methods include, but are not limited to, vacuum filtration, separatory extraction, or distillation. A preferred method is filtration using air or liquid, but other methods will be apparent to those skilled in the art.

If any products require further washing with organic solvents to separate impurities, reaction intermediates, or byproducts can be done according to methods known in the art. Suitable organic solvents include, but are not limited to, ether, methanol, ethanol, ethyl acetate, or hexanes. Other types of solvents will be apparent to those skilled in the art. Any organic solvent should be evaporated using methods known in the art. Evaporation methods may be accomplished at room temperature, by vacuum, aspiration, or by using latent heat. The evaporation methods are not limited to these techniques and other techniques will be apparent to those skilled in the art.

The reaction product may require purification. This may be accomplished using purification techniques known in the art. These techniques include, but are not limited to, column chromatography, flash chromatography, recrystillization, or gel chromatography. Flash chromatography on silica gel is preferred but other methods will be apparent to those skilled in the art. Any organic solvents suitable for chromatography may be used. These include, but are not limited to, methanol, acetonitrile, hexanes, carbontrichloride, and ethyl acetate. Other solvents will be apparent to those skilled in the art and may be used without detracting from the spirit of the invention.

Generally, nucleotides of the invention may be prepared by protecting the 5' position of the sugar moiety of the imidazole ring and derivatizing the 3' position with an appropriate phosphoramidite or other activated phosphate suitable for use on a DNA synthesizer.

Alkylation of the imidazole active methylene with α-halo-α-[reactive functionality]acetaldehyde dimethylketal or α-halo-methyl-[reactive functionality]ketone with subsequent amination provides imidazole carboxamides. These can be converted to 5'-DMT-3'-cyanoethylphosphoramidites and inserted into sequence specific oligonucleotides. The prepared oligonucleotides, which are in blocked form, are removed from the solid support upon which they are elaborated such as by ammonium hydroxide treatment. Basic treatment as above removes the oligonucleotides from the solid support and cyclizes the imidazole moiety to a 3-deaza-3-[reactive functionality]-guanine residue with the desired oligonucleotide sequence. Further cyclization between the resulting N-2-exocyclic amine group and the aldehydic or ketonic carbonyl provides tricyclic heterocycle with reactive functionality, (pyrrolo[2,3-β]-imidazo[2,3-δ]pyridin-2-one (5H)-7-(or 8)-[reactive functionality]). Alternately, cleavage from the support with concentrate ammonium hydroxide directly cyclizes the imidazole carboxamide to the 3-deazaguanine.

Direct deoxyribosylation of 6-isobutryl pyrrolo[2,3-]imidazo[2,3-δ]pyridine 7-(or 8)-[reactive functionality] provides the 1-(2'-deoxy-β-D-erythro-pentofuransyl) derivative after basic deblocking of the toluoyl groups. The tricyclic heterocycle can be obtained from the alkylation of the tetrahydropyranyl derivative of methyl 5-cyanomethylimidazole 4-carboxylate in accordance with the procedure of the *Journal of Medicinal Chemistry*, Vol. 21, p. 1212 (1978), with α-halo-α-[reactive functionality]-acetaldehyde dimethyl-ketals or α-halomethyl-[reactive functionality] ketones with subsequent amination. Acid treatment removes the tetrahydropyranyl blocking group and reducing conditions provides the 7,8-di-hydro 7-(or 8)-[reactive functionality] tricyclic heterocycle. The dihydropyrrole ring nitrogen can be protected with an isobutryl group. The 5'-DMT-3'-phosphoramidite-6-isobutryl nucleoside can be inserted into sequence-specific oligonucleotides via standard automated synthesis. oligonucleotides prepared in this manner contain a pyrrolo[2,3-b]imidazo[2,3-d]-pyridin-4-one(5H)-7-(or 8)-[reactive functionality], the 7,8-dihydro ring replacing a normal guanine residue.

In another aspect of the invention, oligonucleotides or oligonucleotide analogs incorporating the novel compounds of the invention are provided. Generally, the oligonucleotides or oligonucleotide analogs may comprise a sugar modified or native oligonucleotide containing a target sequence that is specifically hybridizable with a preselected nucleotide sequence, a sequence of DNA or RNA that is involved in the production of proteins whose synthesis is ultimately to be modulated or inhibited in entirely, of single stranded or double stranded DNA or RNA molecule and which is nuclease resistant.

Oligonucleotides or oligonucleotide analogs incorporating the novel compounds of the invention may be synthesized, conveniently through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide of reasonable length which may be desired. An oligonucleotide or oligonucleotide analog may then be constructed on a synthesizer incorporating one or more of the 5-cyano-[reactive substituent]-methyl imidazole compounds in its sequence.

The resulting novel oligonucleotides or oligonucleotide analogs are synthesized by the standard solid phase, automated nucleic acid synthesizer such as the Applied Biosystems, Incorporated 380B or MilliGen/Biosearch 7500 or 8800. Triester, phosphoramidite, or hydrogen phosphonate coupling chemistries, M. Caruthers, *oligonucleotides. Antisense Inhibitors of Gene Expression.*, pp. 7–24, J. S. Cohen, ed. (CRC Press, Inc. Boca Raton, Fla., 1989), are used in with these synthesizers to provide the desired oligonucleotides or oligonucleotide analogs. The Beaucage reagent, *Journal of American Chemical Society*, Vol. 112, pp. 1253–1255 (1990) or elemental sulfur, S. Beaucage et al., *Tetrahedron Letters*, Vol. 22, pp. 1859–1862 (1981), is used with phosphoramidite or hydrogen phosphonate chemistries to provide substituted phosphorothioate oligonucleotides.

The oligonucleotides or oligonucleotide analogs may further comprise a reactive portion appended to the novel base portion; this reactive functionality may be attached to the base with a tether group. For example, the oligonucleotide or oligonucleotide analogs may further comprise a reactive portion capable of catalyzing, alkylating, or otherwise effecting the cleavage of RNA, especially of its phosphodiester bonds. This reactive portion may be connected to the targeting portion by a tether. The reactive functionalities may either be basic, acidic, or amphoteric. Heteroatomic species can be formulated to be either basic or acidic or, indeed, to be amphoteric for such purposes. Alkylating and free radical forming functionalities may also be used for these purposes. These functionalities are disclosed as set forth in PCT Application Number PCT\US91\00243 assigned to a common assignee hereof, entitled "Compositions and Methods for Detecting and Modulating RNA Activity and Gene Expression," the disclosures of which are incorporated herein by reference to disclose more fully such functionalities.

These oligonucleotide compositions comprise a targeting portion specifically hybridizable with a preselected nucleotide sequence of RNA, some of the phosphodiester bonds may be substituted with a structure that functions to enhance the compositions' ability to penetrate into cells' intracellular region where the RNA, whose activity is to be modulated, is located. Such substitutions comprise phosphorothioate bonds, short chain alkyl, cycloalkyl structures, structures that are substantially non-ionic and non-chiral. Phosphodiester bond modifications are disclosed as set forth in U.S. patent applications assigned to a common assignee hereof, entitled "Backbone Modified Oligonucleotide Analogs," Ser. No. 07/703,169 and "Heteroatomic oligonucleotide Linkages," Ser. No. 07/903,160, the disclosures of which are incorporated herein by reference to disclose more fully such modifications. Backbone modifications may be used without departing from the spirit of the invention.

As will be appreciated by persons of ordinary skill in the art, variations in the structures of the sugar moieties useful in the preparation of the subject compositions may be made without deviating from the spirit of the invention. Suitable substituents on the sugar moiety inlcude, but are not limited to, O,H, lower alkyl, substituted lower alkyl, aralkyl, heteroalkyl, heterocycloalkyl, amino-alkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH_2$, $OCH_2CCH$, OCCHO, or an RNA cleaving moiety. Generally, substituted sugars may be synthesized according to methods disclosed in PCT Patent Application Number PCT\US91\00243 assigned to a common assignee hereof, entitled "Compositions and Methods for Detecting and Modulating RNA Activity and Gene Expression," the disclosures of which are incorporated herein by reference to fully disclose such modifications. See also Motawai, supra.

Once again, it is not necessary that every sugar linking function be in a modified form a substantial number and even a predominance of such linking groups may exist in the native, phosphodiester form as long as the overall targeting portion of the compositions of the molecules exhibits an effective ability to penetrate into the intracellular spaces of cells of the organism in question or otherwise to contact the target RNA and to specifically bind therewith to form a hybrid capable of detecting and modulating the RNA activity. Of course, fully unmodified, native phosphodiester structure as well.

Modifications that may provide oligonucleotides or analogs that are substantially less ionic than native forms and facilitate penetration of modified or unmodified oligonucleotides into the intracellular spaces are also contemplated by this invention. Any of the existing or yet to be discovered methods for accomplishing this goal may be employed in accordance with the practice of the present invention. As will be appreciated by those skilled in the art, modifications of the phosphate bond find utility in this regard. Variations in the phosphate backbone useful in the preparation of the subject compositions may be made without deviating from the spirit of the invention. Modifications at the phosphorous atom are set forth in an application having U.S. Ser. No. 07/558,663 and assigned to a common assignee hereof, said application being entitled "Polyamine Oligonucleotides to Enhance Cellular Uptake," filed Jul. 27, 1990 the modification of the sugar structure including the elimination of one of the oxygen functionalities may permit the introduction of such substantially non-chiral, non-ionic substituents in this position.

Standard backbone modifications such as substituting P for S, Me—P, MeO—P, $H_2N$—P, etc. These substitutions are thought in some cases to enhance the sugar modified oligonucleotide properties. Such substitutions include, but are not limited to, phosphorothionate, methyl phosphonate, or alkyl phosphate. Backbone modifications are disclosed as set forth in U.S. patent applications assigned to a common assignee hereof, entitled "Backbone Modified Oligonucleotide Analogs," Ser. No. 07/703,619 and "Heteroatomic Oligonucleotide Linkages," Ser. No. 07/903,160, the disclosures of which are incorporated herein by reference in order to disclose more fully such modifications. The entirety of the disclosure of these applications are incorporated herein by reference in order to disclose more fully such modifications.

The present invention is further described in the following examples. These examples are for illustrative purposes only, and are not to be construed as limiting the appended claims.

EXAMPLE 1

Chromatography and Purification

Silica gel used for flash chromatography was ICN 60 (Costa Mesa, Calif.), 32–63 mesh. Materials not soluble in the solvent system used for flash chromatography (FC) were co-evaporated onto E. Merck silica gel loo (Darmstadt, Republic of Germany), 70–230 mesh, using a suitable solvent. The dry materials were then applied to the top of a FC column. TLC was performed on prescored E. Merck Kieselgel 60 $F_{254}$ plates. Compounds were visualized by illuminating TLC plates under UV light (254 nm) and/or by spraying with 10 methanolic $H_2SO_4$ followed by heating. Evaporations were carried out at 40–50° C. using a rotary evaporator and a vacuum pump coupled to a vacuum controller. $^1$H-NMR spectra were obtained at 400 mHz in dmso-$d_6$ unless otherwise noted. Where relevant, treatment of samples with $D_2O$ recorded exchangeable protons. Infrared spectra were recorded on a Perkin-Elmer 16PC FT-IR spectrophotometer. Solvent system A=ethyl acetate-hexanes, 3:2; B=ethyl acetate-methanol, 9:1, v/v.

EXAMPLE 2

Synthesis of Methyl 5-(cyanomethyl)-1-(2'-deoxy-3, 5-di-O-p-toluoyl-β-D-erythro-pentofuranosyl) imidazole-4-carboxylate A large scale synthesis of the methyl 5-(cyanomethyl)-1-(2'-deoxy-3,5-di-O-p-toluoyl-β-D-erythro-pentofuranosyl) imidazole-4-carboxylate, a starting material for this work was carried out according to the sodium-salt glycosylation procedure described in Revenkar, supra.

EXAMPLE 3

Synthesis of Methyl 5-(cyanomethyl)-3-tetrahydropyranyl-imidazole-4-carboxylate

Methyl 5-cyanomethyl-3-tetrahydropyranyl-imidazole-4-carboxylate was prepared and separated from its positional isomer according to the procedure described in Cook, J. Med. Chem., supra.

EXAMPLE 4

Synthesis of 2'-deoxy-3-deazaguanosine (6-amino-1-(2-deoxy-β-D-erythro-pentofuranosyl)imidazo[4,5-c]pyridin-4(5H)-one A small scale synthesis of the 2'-deoxy-3-deazaguanosine (6-amino-1-(2-deoxy-β-D-erythro-pentofuranosyl) imidazo

[4,5-c]pyridin-4(5H)-one yielded material identical in every respect with that reported in Revenkar, supra. The alkylation procedures described below yield diastereomeric mixtures differing in configuration at the alkylated (methene) carbon. For the nucleosides, these mixtures exhibit well-resolved signals for their H-2, methene, H1' and other protons in their 400 mHz $^1$H-NMR spectra.

EXAMPLE 5

General Nucleoside Alkylation Method. Methyl 5-(cyano[nonyl]methyl)-1-(2'-deoxy-3,5-di-O-p-toluoyl-β-D-erythro-pentofuranosyl)imidazole-4-carboxylate A solution of methyl 5-(cyanomethyl)-1-(2'-deoxy-3,5-di-O-p-toluoyl-β-D-erythro-pentofuranosyl) imidazole-4-carboxylate (5.7 g, 11 mmol) in anhydrous acetonitrile (75 mL) was treated with sodium hydride (0.88 g, 60% in oil, washed with hexanes) at room temperature and under an atmosphere of argon. This suspension was stirred for 15 minutes and then treated with iodononane (7.5 mL, 37.4 mmol) via syringe. The reaction mixture was stirred under these conditions for 6 hr; thin layer chromatography showed the disappearance of starting material nucleoside (Rf=0.45, solvent A) and the appearance of two closely migrating and faster products (Rf=0.65, avg). The reaction was quenched with the addition of glacial acetic acid to pH 5 and then evaporated to dryness in vacuo to afford a yellow syrup. The syrup was redissolved in dichloromethane (150 mL) and the solution was washed with cold 0.1 N HCl, water, and then dried over magnesium sulfate. Filtration and evaporation of the organic layer afforded a yellow gum which was purified using FC on silica gel (120 g) using a gradient of ethyl acetate in hexanes (20 to 50%). Fractions corresponding to the alkylated products were pooled and evaporated to yield Methyl 5-(cyano[nonyl]methyl)-1-(2'-deoxy-3,5-di-O-p-toluoyl-β-D-erythro-pentofuranosyl)imidazole-4-carboxylate as a foam, 2.9 g (47%). $^1$H-NMR: δ,8.18 and 8.15 (s,s; 1 H; H-2); 6.48 and 6.37 (t,t; 1 H; H1'); 4.68 and 4.36(2 m, 1 H, methene); 3.32 (s, 3H, COOCH$_3$); 2.05, 1.75, 1.18 and 0.90(4 m; 19 H; nonyl). IR (film): 2240 cm$^{-1}$ (CN). Anal. Calcd for C37H45N3O7 (643.778): C, 69.03, H, 7.04, N, 6.53. Found: C, 68.77, H, 6.97, N, 6.39.

The bulkiest 3-C substituent on the 3-deazapurine ring system induces the compounds into an unnatural 3'-endo/high-anti (-sc) conformation. Two-dimensional NMR experiments (2D-NOESY) indicate that substituted 2'-deoxy-3-deazaguanosines prefer the anti-conformation. The bulky substituent in 2'-deoxy-3-(2-[1-naphthyl]ethyl)-3-deazaguanosine appears to force the sugar into an unusual 3'-endo conformation. Gradually decreasing the size of these substituents is expected to increase the equilibrium population of the sugar towards 2'-endo. These structural changes may be correlated with biological activity; it is reasonable to expect that the 2'-deoxy-3-alkyl(aryl)-3-deazapurines might be enhanced substrates for viral kineses due to their preference for the anti-conformation.

The 2'-deoxy-3-alkyl(aryl)-3-deazaguanosines have uv spectra with nearly identical maxima to that of 2'-deoxy-3-deazaguanosine. Also, their proton NMR exhibit H-2 (IUPAC numbering) aromatic resonances at δ7.9 to 8.0 ppm, compared to 7.9 ppm for 2'deoxy-3-alkyl(aryl)-3-deazaguanosines, evidence of the nearly negligible electronic contributions from these alkyl or aryl substitutions to the overall purine ring current. However, the 2D-NOESY NMR spectrum of 2'-deoxy-3-(2-[1-naphthyl]ethyl)-3-deazaguanosine, (7-(2-[1-naphthyl]ethyl)-6-amino-1-(2deoxy-β-D-erythro-pentofuranosyl) imidazo[4,5)-c]pyridin-4(5H)-one, in dmso-d reveals some interesting features. Poonian, supra. The cross-peaks for the imidazole H-2 and sugar H-3'-protons are strong and there are weak cross peaks for the H-2 and H-2' protons. In addition, the H-2" (α) signal appears upfield of the H-2' (β) signal, a configuration not normally registered for 2'-deoxynucleosides. Taken together, these observations indicate that the pseudorotation, Saenger, supra, of the sugar strongly favors 3'-endo (75%) and that this conformation forces the H-2" proton into the shielding volume of the heterocyclic rings. The relative populations of 2' and 3-endo conformations of the nucleosides were determined from their 2D-NOESY spectrum, by measurement of the volume of the cross peaks of H-2 and H-2' (β) versus H-2 and H-3' and divided by the sum of both cross peak volumes. An absence of NOE signals for the N—H imino and 3'-protons indicate that this and other nucleosides in this series appear to exist strictly in an anti conformation. Rosenmeyer, et al., *J. Org. Chem.*, 1990, 55, 5784. Further, because there is a strong NOE signal from H-2 and H-1', it appears that this nucleoside is virtually locked into a high-anti (-sc) conformation. In contrast, the 2D-NOESY spectrum for the 2'-deoxy-3-allyl-3-deazaguanosine (7-allyl-amino-1-(2-deoxy-β-D-erythro-pentofuranosyl) imidazo[4,5c]pyridin-4 (5H)-one) exhibits strong cross-peaks for the imidazole H-2 and sugar H-2' protons and lesser cross peaks for H-2 and H-3', indicating 2'-endo (62%) as a predominant conformation for the deoxyribose sugar.

EXAMPLE 6

Synthesis of Methyl 5-(allyl[cyano]methyl)-1-(2'deoxy-3,5-di-O-p-toluoyl-β-D-erythro-pentofuranosyl)imidazole-4-carboxylate A solution of methyl 5-(cyanomethyl)-1-(2'-deoxy-3,5-di-O-p-toluoyl-β-D-erythro-pentofuranosyl) imidazole-4-carboxylate (5.0 g, 9.7 mmol) in anhydrous acetonitrile (75 mL) was treated with sodium hydride (0.46 g, 11.6 mmol) and then allyl bromide (2.5 mL, 29 mmol). Workup of the reaction and purification of the products on silica gel (75 g) as described in Example 1 afforded methyl 5-(allyl[cyano]methyl)-1-(2'deoxy-3,5-di-O-p-toluoyl-β-D-erythro-pentofuranosyl)imidazole-4-carboxylates a yellowish foam, 3.7 g (68%). $^1$H-NMR (200 mHz): δ,8.15 and 8.13 (s,s; 1 H; H-2); 6.38 (m, 1H; H1'); 5.75 and 5.08 (2m; 3H; vinyl); 3.79 (s, 3H, COOCH$_3$). Anal. Calcd for C$_{32}$H$_{31}$N$_3$O$_7$ (557.60): C, 66.77, H, 5.60, N, 7.53. Found: C, 66.43; H, 5.59, N, 7.38.

EXAMPLE 7

Synthesis of Methyl 5-(benzyl[cyano]methyl)-1-(2'-deoxy-3,5di-O-p-toluoyl-β-D-erythro-pentofuranosyl)imidazole-4-carboxylate A solution of methyl 5-(cyanomethyl)-1-(2'-deoxy-3,5-di-O-p-toluoyl-β-D-erythro-pentofuranosyl)imidazole-4-carboxylate (5.0 g, 9.6 mmol) in anhydrous acetonitrile (75 mL) was treated with sodium hydride (0.46 g, 11 mmol) under argon and stirred at room temperature for 15 minutes. The mixture was cooled to 4° C. in an ice bath and a solution of benzyl bromide (1.26 mL, 10.6 mmol) in acetonitrile (15 mL) was added dropwise over 70 min. The ice bath was removed and the reaction further stirred at room temperature for 2.5 hours. Workup of the reaction and purification of the products on silica gel (100 g) as described in the Example 1 afforded methyl 5-(benzyl[cyano]methyl)-1-(2'-deoxy-3, 5di-O-p-toluoyl-β-D-erythro-pentofuranosyl)imidazole-4- carboxylate as a white foam, 3.4 g (58%). $^1$H-NMR: δ,8.12 and 8.05 (s,s; 1H; H-2); 8.0–7.10 (m, 13 H; aromatic); 6.33 and 6.01 (t,t; 1H; H-1'); 5.22 and 5.02 (t,t; 1H; methene); 3.80 (s, 3H, COOCH$_3$). IR (film): 2240 cm$^{-1}$ (nitrile). Anal. Calcd for C$_{35}$H$_{33}$N$_3$O$_7$ (607.66): C, 69.18; H, 5.47; N, 6.92. Found: C, 69.15; H; 5.43; N, 6.82.

EXAMPLE 8

Synthesis of Methyl 5-(cyano[2-(1-naphthyl)ethyl]methyl)-1-(2-deoxy-3,5di-O-p-β-D-erythro-pentofuranosyl)imidazole-4-carboxylate A solution of methyl 5-(cyanomethyl)-1-(2'-deoxy-3,5-di-O-p-toluoyl-β-D-erythro-pentofuranosyl)imidazole-4-carboxylate (7.43 g, 14.3 mmol) in anhydrous acetonitrile (50 mL) was treated with sodium hydride (1.15 g, 28.7 mmol) under argon and stirred at room temperature for 15 minutes. The 2-(1-naphthyl)ethyl bromide (16.9 g, 71.5 mmol) was added neat and the reaction stirred for 18 hours. Workup of the reaction as described in Example 5 and purification of the products on silica gel (150 g), as described in Example 1, using a gradient of ethyl acetate in hexanes (20 to 60%) yielded three major fractions. Fraction 1(1.55 g) contained the faster isomer; fraction 2(0.90 g) contained a mixture of both isomers; fraction 3(1.53 g) contained the slower isomer. Overall yield of methyl 5-(cyano[2-(1-naphthyl)ethyl]methyl)-1-(2-deoxy-3,5 di-O-p-β-D-erythro-pentofuranosyl) imidazole-4-carboxylate, 3.9 g, 42%. Fraction 1. $^1$H-NMR: δ,8.17 (s, 1H, C(2)-H); 7.9–7.1 (m, 15H, aromatic); 6.38 (t, 1H, H-1'); 5.17 (t, 1H, methene); 3.72 (s, 3H, COOCH$_3$). Fraction 3. δ,8.15 (s, 1H, H-2); 7.9–7.1 (m, 15H, aromatic); 6.26 (t, 1H, H-1'); 4.82 (t, 1H, methene); 3.77 (s, 3H, COOCH$_3$). Anal. Calcd for C$_{40}$H$_{37}$N$_3$O$_7$ (671.75): C, 71.52; H, 5.55; N, 6.26. Found: C,71.76; H, 5.54; N, 6.02.

EXAMPLE 9

General Ammonolysis Method. 5-(Cyano[nonyl]methyl)-1-(2'deoxy-β-D-erythro-pentofuranosyl)imidazole-4-carboxamide The nucleoside methyl 5-(cyano[nonyl]methyl)-1-(2'-deoxy-3,5-di-O-p-totuoyl-β-D-erythro-pentofuranosyl)imidazole-4-carboxylate (2.98 g, 4.6 mmol) was dissolved in anhydrous methanol (5 mL) and transferred to a stainless steel bomb. The solution was cooled to −78° C. and then treated with anhydrous liquid ammonia (45 mL). The bomb was sealed and then heated to 100° C. in an oil bath for 21 hours. TLC (solvent B) exhibited products Rf=0.45, and toluamide Rf=0.85, indicating a complete removal of the toluoyl protecting groups. Ammonia was evaporated at room temperature and the amber gum which resulted was flash chromatographed on silica gel (80 g) using a gradient of methanol in ethyl acetate (5 to 10%). Fractions corresponding to the products were pooled and evaporated in vacuo to yield 5-(Cyano[nonyl]methyl)-1-(2'deoxy-β-D-erythro-pentofuranosyl)imidazole-4-carboxamide as a white foam, 1.2 g (63%). $^1$H-NMR: δ,8.09. and 8.05 (s,s; 1H; H-2); 6.14 (t, 1H; H1'); 5.45 and 5.32(2 dd, 1H, methene); 2.10,1.80, 1.40–1.05 and 0.82(4m, 19H; nonyl). Anal. Calcd. for C20H32N4O4 (392.50): C, 61.20; H, 8.22; N, 14.27. Found: C, 60.97; H, 8.24; N, 13.98.

EXAMPLE 10

Synthesis of 5-(Allyl[cyano]methyl)-1-(2'-deoxy-β-D-erythro-pentofuranosyl)-imidazole-4 carboxamide The nucleoside methyl 5-(allyl[cyano]methyl)-1-(2'deoxy-3,5-di-O-p-toluoyl-β-D-erythro-pentofuranosyl) imidazole-4-carboxylate (3.95g, 7.08 mmol) was treated with liquid ammonia and heated to 100° C. in a stainless steel bomb for 8 hours. The products of this reaction were worked up and purified on silica gel (80 g) as described in Example 1. The deprotected compound 5-(allyl[cyano]methyl)-1-(2'-deoxy-β-D-erythro-pentofuranosyl)-imidazole-4 carboxamide was isolated as a white foam, 1.3 g (58%). $^1$H-NMR: δ,8.09 and 8.05 (s,s; 1 H; H-2); 6.15 (t, 1 H; H1'); 5.75 and 5.10 (2 m, 3 H; vinyl); 5.42 and 5.34 (t,t; 1 H; methene). Anal. Calcd for C$_{14}$H$_{18}$N$_4$O$_4$ (306.33): C, 54.89; H, 5.92; N, 18.29. Found: C, 54.58; H, 5.92; N, 17.93.

EXAMPLE 11

Synthesis of 5-(Benzyl[cyano]methyl)-1-(2'-β-D-erythro-pentofuranosyl)-imidazole-4-carboxamide The nucleoside methyl 5-(benzyl[cyano]methyl)-1-(2'-deoxy-3,5di-O-p-toluoyl-β-D-erythro-pentofuranosyl)imidazole-4-carboxylate (3.0 g, 4.93 mmol) was treated with liquid ammonia and heated to 100° C. in a stainless steel bomb for 6 hours. The products of this reaction were worked up and purified on silica gel (80 g) as described in Example 1. The deprotected compound 5-(benzyl[cyano]methyl)-1-(2'-β-D-erythro-pentofuranosyl)-imidazole-4-carboxamide was isolated as a white foam, 1.0 g (59%). $^1$H-NMR: δ,8.05 and 8.03 (s,s; 1H; H-2); 7.25 (m; 5H; phenyl); 6.17 and 6.07 (t,t; 1H; H1'); 5.50 and 5.42 (t,t; 1H; methines). Anal. Calcd for C$_{18}$H$_{33}$N$_3$O$_7$ (357.39): C, 60.49; H, 5.92; N, 15.68. Found: C, 60.65; H, 5.69; N, 15.23.

EXAMPLE 12

Synthesis of 5-(Cyano[2-(1-naphthyl)ethyl]methyl)-1-(2deoxy-β-D-erythro-pentofuranosyl)-imidazole-4-carboxamide The nucleoside methyl 5-(cyano[2-(1-naphthyl) ethyl]methyl)-1-(2-deoxy-3,5di-O-p-β-D-erythro-pentofuranosyl)imidazole-4-carboxylate (3.78 g, 5.76 mmol) was treated with liquid ammonia and then heated to 100° C. in a stainless steel bomb for 20 hours. The products of this reaction were worked up and purified on silica gel (86 g) as described in Example 1. The deprotected compound 5-(cyano[2-(1-naphthyl)ethyl]methyl)-1-(2deoxy-β-D-erythro-pentofuranosyl)-imidazole-4-carboxamide was isolated as a white foam, 1.2 g (49%). $^1$H-NMR: δ,8.14 and 8.08 (s,s; 1H; H-2); 8.0–7.3 (m, 7H; naphthyl); 6.22 and 6.19 (t,t; 1H; H1'); 5.55 and 5.30 (t,t; 1H, methene). Anal. Calcd for C$_{23}$H$_{24}$N$_4$O$_4$ (420.47): C, 65.70; H, 5.75; N, 13.32. Found: C, 65.78; H, 5.72; N, 13.05.

EXAMPLE 13

General Cyclization Method. 6-Amino-7-nonyl-1-(2-deoxy-β-D-erythro-pentofuranosyl)imidazo[4,5-c]pyridin-4(5H)-one (2'-Deoxy-3-nonyl-3-deazaguanosine)

A solution of the nucleoside 5-(cyano[nonyl]methyl)-1-(2'deoxy-β-D-erythro-pentofuranosyl)imidazole-4-carboxamide (250 mg) in 35 mL methanolic ammonia (saturated at −20° C.) was heated to 95° C. in a sealed vessel for 18 hours. The mixture was evaporated to afford a dark solid which was redissolved in hot ethanol. The solid which separated upon cooling was filtered and dried in vacuo for 18 hours to afford 2'-Deoxy-3-nonyl-3-deazaguanosine (180 mg, 72%) as an amorphous solid. MP 150° C. dec. $^1$H-NMR: δ,10.3 (bs, 1H, N—H); 7.90 (s, 1H, H-8); 6.08 (pseudo t, 1H, H-1', J=6.0 Hz); 5.15 (bs, 2H, NH$_2$); 2.52, 1.30 and 1.82(3 m, 19H, nonyl). UV, $^\lambda$max,$^{nm}$, (log ε): MeOH, 312(4.001), 278(4.040); pH 1, 322(3.687), 296 (3.845); pH 7, 308 (2.811), 276(2.842); pH 12,290(3.978). Anal. Calcd for C$_{20}$H$_{32}$N$_4$O$_4$ (392.50): C, 61.20; H, 8.22; N, 14.27. Found: C, 61.02; H, 8.20; N, 14.22.

EXAMPLE 14

Synthesis of 7-Allyl-6-amino-1-(2deoxy-β-D-erythro-pentofuranosyl)imidazole [4,5-c]pyridin-4-(5H)-one (2'-deoxy-3-allyl-3-deazaguanosine)

The nucleoside 5-(Allyl[cyano]methyl)-1-(2'-deoxy-β-D-erythro-pentofuranosyl)-imidazole-4 carboxamide (250 mg) was cyclized and purified according to the procedure described in Examples 13 and 1, respectively, to yield 7-Allyl-6-amino-1-(2deoxy-β-D-erythro-pentofuranosyl) imidazole [4,5-c]pyridin-4-(5H)-one (2'-deoxy-3-allyl-3-deazaguanosine) (190 mg, 76%) as an amorphous solid. MP.155° C. dec. $^1$H-NMR (200 mHz): δ,10.4 (bs, 1H, N—H); 7.98 (s, 1H, H-8); 6.05 (pseudo t, 1 H, H1', J=5.4 Hz); 5.92, 5.02 and 4.88 (3m, 3H, vinylic); 5.34 (s, 2H, NH$_2$); 3.40 and 3.19 (2m, 2H, allylic). UV, $^\lambda$max,$^{nm}$, (log ε): 310 (3.996), 276 (4.060); pH 1, 320 (3.891), 292, (4.064); pH 7, 306 (3.963), 274 (4.011); pH 12, 288 (4.160). Anal. Calcd for C$_{14}$H$_{18}$N$_4$O$_4$ (306.32): C, 54.89; H, 5.92; N, 18.29. Found: C, 54.58; H, 5.92; N, 18.09.

EXAMPLE 15

Synthesis of 6-Amino-7-benzyl-1-(2-deoxy-β-D-erythro-pentofuranosyl) imidazo-[4,5c]pyridin 4 (5H)-one (2'-deoxy-3-benzyl-3-deazaguanosine The nucleoside 5-(Benzyl[cyano]methyl)-1-(2'-β-D-erythro-pentofuranosyl)-imidazole-4-carboxamide (250 mg) was cyclized and purified by trituration with hot ethanol as described in Examples 13 to yield 2'-deoxy-3-benzyl-3-deazaguanosine (200 mg, 80%) as a white solid. MP 140° C. dec. $^1$H-NMR: δ 10.4 (bs, 1H, N—H); 7.84 (s, 1H, H-8); 7.3–7.1 (m, 5H, phenyl); 6.04 (pseudo t, 1H, H-1', J=6.3 Hz); 5.07 (bs, 2H, NH$_2$); 4.07 and 3.88 (dd, 2H, benzylic, J=17 Hz). UV, $^{\lambda max,nm}$, (log ε): MeOH, 310 (3.950), 276 (4.002); pH 1, 320 (3.835), 294 (3.988); pH 7 308 (3.923), 274 (3.959); pH 12,310 (3.930). Anal. Calcd for C$_{18}$H$_{20}$N$_4$O$_4$ (356.38): C, 60.66; H, 5.66; N, 15.72. Found: C, 60.15; H, 5.60; N, 15.51.

EXAMPLE 16

Synthesis of 6-Amino 7-(2-[1-naphthyl]ethyl)-1-(2deoxy-β-D-erythro-pentofuranosyl)imidazo[4,5-c] pyridin-4(5H)-one (2'-deoxy-3-(2-[1-naphthyl]ethyl) 3-deazaguanosine.

The nucleoside 5-(Cyano[2-(1-naphthyl) ethyl]methyl)-1-(2deoxy-β-D-erythro-pentofuranosyl)imidazole-4-carboxamide (250 mg) was cyclized and purified from hot ethanol as described in Example 13 to yield 6-Amino 7-(2-[1-naphthyl]ethyl)-1-(2deoxy-β-D-erythro-pentofuranosyl) imidazo[4,5-c]pyridin-4(5H)-one (2'-deoxy-3-(2-[1-naphthyl]ethyl)3-deazaguanosine (200 mg, 80%) as an off-white solid. MP 195° C. dec. $^1$H-NMR: δ,10.5 (bs, 1H, N—H); 7.98 (s, 1H, H-8); 8.2–7.4 (m, 7H, naphthyl); 6.21 (pseudo t, 1H, H-1', J=6.9 Hz); 5.32 (bs, 2H, NH$_2$); 3.3–2.8 (m, 4H, ethylene). UV $^\lambda$max,$^{nm}$, (log ε): MeOH, 310(4.019), 289(4.180); pH 1,324(3.805), 290 (4.114); pH 7,310 (3.611), 284(3.834); pH 12,286(4.185). Anal. Calcd for C$_{23}$H$_{24}$N$_4$O$_4$ (420.47): C, 65.70; H, 5.75; N, 13.32. Found: C, 65.80; H, 5.72; N, 13.05.

EXAMPLE 17

General Heterocycle Alkylation Method. Methyl 5-(cyano[nonyl]methyl)-3-tetrahydropyranyl-imidazole-4-carboxylate The cyanomethyl imidazole (5.0 g, 20 mmol) was alkylated using NaH (1.2 g, 60% in oil, washed with hexanes) and iodononane (7.6 g, 30 mmol) as described in Example 5, the General Procedure for the nucleosides. The products were purified by FC using a gradient of ethyl acetate in hexanes (20 to 50%). Evaporation of the fractions containing the products yielded methyl 5-(cyano[nonyl]methyl)-3-tetrahydro-pyranyl-imidazole-4-carboxylate (5.0 g, 67%) as a yellow foam. $^1$H-NMR (200 mHz): δ,8.22 (s, 1H, H-2); 5.87 (m, 1 H, H-2' tetrahydropyranyl); 4.58 (m, 1H, methene); 3.85 (s, 3H, COOCH$_3$); 1.30 and 0.88(2 m, 19H, nonyl). Anal. Calcd for C$_{21}$H$_{33}$N$_3$O$_3$ (375.51): C, 67.17; H, 8.86; N, 11.19. Found: C, 67.47; H, 8.95; N, 11.21.

EXAMPLE 18

Synthesis of Methyl 5-(allyl[cyano]methyl)-3-tetrahydro-pyranyl-imidazole-4-carboxylate The cyanomethyl imidazole (5.0 g, 20 mmol) was alkylated using NaH (1.2 g) and allyl bromide (3.6 g, 30 mmol) and purified according to Examples 5 and 1, respectively. White foam, 3.9 g, 67%. $^1$H-NMR (200 mHz): δ,8.23 (s, 1H, H-2); 5.87 (m, 1H, H-2' tetrahydropyranyl); 5.77 and 5.15 (2m, 3H, vinylic); 5.68 (m, 1H, methene); 3.86 (s, 3H, COOCH$_3$). Anal. Calcd for C$_{15}$H$_{19}$N$_3$O$_3$: C, 62.27; H, 6.62; N, 14.52. Found: C, 62.27; H, 6.62; N, 14.54.

EXAMPLE 19

Synthesis of Methyl 5-(benzyl[cyano]methyl)-3-tetrahydropyranyl-imidazole-4-carboxylate The cyanomethyl imidazole (5.0 g, 20 mmol) was alkylated using NaH (1.2 g) and benzyl bromide (5.1 g, 30 mmol), as described in Example 5, and purified according to Example 1. White foam, 4.8 g, 71%. $^1$H-NMR (200 mHz): δ,8.25 (s, 1H, H-2); 7.29 (m, 5H, phenyl); 6.83 (m, 1H, H-2' tetrahydropyranyl); 4.84 (m, 1H, methene); 3.84 and 3.80 (s,s; 3H, COOCH$_3$); 3.19 (m, 2H, benzylic). Anal. Calcd. for C$_{19}$H$_{21}$N$_3$O$_3$ (339.39): C, 67.24; H, 6.24; N, 12.38. Found: C, 67.21; H, 6.19; N, 12.02.

EXAMPLE 20

Synthesis of Methyl 5-(cyano[2-(1-naphthyl)ethyl] methyl)-3-tetrahydropyranyl-imidazole-4-carboxylate The cyanomethyl imidazole (5.0 g, 20 mmol) was alkylated using NaH (1.2 g) and 2-(1-naphthyl)ethyl bromide (7.1 g, 30 mmol, Frinton Labs, Piscataway, N.J.), as described in Example 5, and purified according to the procedure discussed in Example 1. White foam, 5.0 g, 62%. $^1$H-NMR (200 mHz): δ,8.23 (s, 1H, H-2); 8.1–7.3 (m, 7H, naphthyl); 5.80 (m, 1H, H-2' tetrahydropyranyl); 4.58 (m, 1H, methene); 3.57 (s, 3H, COOCH$_3$). Anal. Calcd for C$_{24}$H$_{35}$N$_3$O$_3$ (403.48): C, 71.44; H, 6.24; N, 10.41. Found: 71.38; H, 6.16; N, 10.45.

EXAMPLE 21

General Nucleoside Cyclization Method. 6-Amino-7-nonyl-1,5-dihydroimidazo[4,5-c]pyridin-4-one Hydrochloride Salt The compound methyl 5-(cyano[nonyl]methyl)-3-tetrahydropyranyl-imidazole-4-carboxylate (2.5 g, 6.7 mmol) was dissolved in 50 mL methanolic ammonia (saturated at −20° C.) in a stainless steel bomb. The mixture was stirred at 75° C. for 72 hours and then evaporated to dryness in vacuo. The resulting solid was co-evaporated with methanol (45 mL) and then immediately stirred with methanolic 1 N HCl (50 mL) for 12 hours. After this time, the reaction mixture was evaporated to afford a light yellow gum. This gum was precipitated by repeated co-evaporation with methanol. Amorphous solid, 1.1 g, 53%. MP 225 darkens; 240° C. dec. $^1$H-NMR: δ,10.8 (bs, 1H, N—H); 8.72 (s, 1H, H-2); 5.80 (bs, 2H, $NH_2$); 2.0, 0.9 and 0.4(3m, 19H, nonyl). UV, $\lambda max,^{nm}$, (log ε): MeOH, 310(3.935), 270 (3.969). Anal. Calcd. for $C_{15}H_{25}N_4OCl$ (312.84): C, 57.59; H, 8.05; N, 17.90. Found: C, 57.53; H, 8.05; N, 17.87.

EXAMPLE 22

Synthesis of 7-Allyl-6-amino-1,5-dihydroimidazo[4,5-c]pyridin-4-one Hydrochloride Salt The compound methyl 5-(allyl[cyano]methyl)-3-tetrahydropyranyl-imidazole-4-carboxylate (2.5 g, 8.6 mmol) was cyclized and isolated according to the procedure discussed in Example 21. Amorphous solid, 1.3 g, 67%. MP 210° C. dec. $^1$H-NMR: δ,11.0 (bs, 1 H, NH); 8.49 (s, 1H, H-2); 5.80 and 4.98(2m, 3H, vinylic); 5.80 (bs, 2H, $NH_2$); 3.26 (m, 2H, allylic). UV, $\lambda max,^{nm}$, (log ε): MeOH, 310 (3.927), 268 (3.985). Anal. Calcd for $C_9H_{11}N_4OCl$ (226.66): C, 47.69; H, 4.89; N, 24.72. Found: C, 48.04; H, 5.02; N, 23.76.

EXAMPLE 23

Synthesis of 6-Amino-7-benzyl-1,5-dihydroimidazo[4,5c]pyridin-4-one Hydrochloride Salt The compound methyl 5-(benzyl[cyano]methyl)-3-tetrahydropyranyl-imidazole-4-carboxylate (2.5 g, 7.4 mmol) was cyclized and isolated according to the procedure described in Example 21. Amorphous solid, 1.9 g, 92%. MP 196° C. dec. $^1$H-NMR: δ,11.5 (bs, 1 H, N—H); 9.20 (s, 1H, H-2); 7.17 (m, 5H, phenyl); 6.20 (bs, 2H, $NH_2$); 3.95 (s, 2H, benzylic). UV, $\lambda max,^{nm}$, (log ε): MeOH, 310(3.958), 268 (3.988). Anal. Calcd for $C_{13}H_{13}N_4OCl$ (276.72): C, 56.42; H, 4.73; N, 20.25. Found: C, 56.40; H, 4.71; N, 20.03.

EXAMPLE 24

Synthesis of 6-Amino-7-(2-[1-naphthyl]ethyl)-1,5-dihydro[4,5-c]pyridin-4-one Hydrochloride Salt The compound methyl 5-(cyano[2-(1-naphthyl)ethyl]methyl)-3-tetrahydropyranyl-imidazole-4-carboxylate (2.5 g, 6.2 mmol) was cyclized and isolated according to the procedure described in Example 21. Amorphous solid, 1.64 g, 78%. MP 260 darkens, 273° C. dec. $^1$H-NMR: δ,11.4 (bs, 1H, N—H); 9.20 (s, 1H, H-2); 8.1–7.4 (m, 7H, naphthyl); 6.10 (bs, 2H, $NH_2$); 3.15 and 3,02 (2 m, 4H, ethylene). UV, $\lambda max,^{nm}$, (log ε): MeOH, 308 (3.930), 272 (4.137). Anal. Calcd for $C_{18}H_{17}N_4OCl$ (340.81): C, 63.18; H, 4.95; N, 16.28. Found: C, 63.18; H, 4.95; H, 16.28.

EXAMPLE 25

Synthesis of 6-Amino-1,5-dihydro[4,5-c]pyridin-4-one (3-Deazaguanine) Hydrochloride Salt The compound cyanomethyl imidazole (2.5 g, 10 mmol) was cyclized and the product isolated according to the procedure described in Example 21. This compound gave a satisfactory $^1$H-NMR but proved unstable during purification and did not fit C,H,N analysis as a hydrochloride salt, Hartman, supra: $^1$H-NMR: δ,10.5 (bs, 1H, N—H); 8.18 (s, 1H, H-2); 5.4 (bs, 2H, $NH_2$); 4.6 (s, 1H, H-7).

EXAMPLE 26

Synthesis of Methyl 5-(cyano[nonyl]methyl)-1-(2'-deoxy-3,5-di-O-p-toluoyl-β-D-erythro-pentofuranosyl)imidazole-4-carboaylate A solution of methyl 5-(cyanomethyl)-1-(2'-deoxy-3,5-di-O-p-toluoyl-β-D-erythro-pentofuranosyl)imidazole-4-carboxylate (5.7 g, 11 mmol) in anhydrous acetonitrile (75 mL) was treated with sodium hydride (0.88 g, 60% in oil, washed with hexanes) at room temperature and under an atmosphere of argon. This suspension was stirred for 15 minutes and then treated with iodononane (7.5 mL, 37.4 mmol) using a syringe. The reaction mixture was stirred under these conditions for 6 hr; thin layer chromatography plates (ethyl acetate/hexanes, 3:2, v/v) showed the disappearance of starting material nucleoside and the appearance of two faster migrating products. The reaction was quenched with the addition of glacial acetic acid to pH 5 and then evaporated to dryness in vacuo to afford a yellow syrup. The syrup was dissolved in dichloromethane (150 mL) and the solution was washed with cold 0.1 N HCl, water, and then dried over magnesium sulfate. Filtration of the desiccant and evaporation of the solvent afforded a yellow gum which was flash-chromatographed on silica gel (120 g) using ethyl acetate-hexanes (1:4 then 1:1). Fractions corresponding to the alkylated products were pooled and evaporated to yield Methyl 5-(cyano[nonyl]methyl)-1-(2'-deoxy-3,5-di-O-p-toluoyl-β-D-erythro-pentofuranosyl)imidazole-4-carboxylate. as a yellowish foam, 2.98 g (47%). 1H-NMR ($Me_2SO$-d6): δ, 8.18 and 8.15 (s,s; C-2 H, 1 H); 6.48 and 6.37 (t,t; H-1', 1 H); 1.18 and 0.90 (2 m, nonyl, 19 H).

EXAMPLE 27

Synthesis of Methyl 5-(allyl[cyano]methyl)-1-(2'-deoxy-3,5-di-O-p-toluoyl-β-D-erythro-pentofuranosyl)imidazole-4-carboxylate A solution of methyl 5-(cyanomethyl)-1-(2'-deoxy-3,5-di-O-p-toluoyl-β-D-erythro-pentofuranosyl)imidazole-4-carboxylate (5.0 g, 9.7 mmol) in anhydrous acetonitrile (75 mL) was treated with sodium hydride (0.46 g, 11.6 mmol) and then allyl bromide (2.5 mL, 29 mmol) in the manner described for in Example 29. The reaction was worked up and chromatographed on silica gel (75 g) using the aforementioned solvent system to afford 84 as a yellowish foam, 3.66 g (68%). 1H-NMR ($Me_2SO$-d6): δ, 8.15 and 8.13 (s,s; C-2 H, 1 H); 6.38 (m, H-1', 1 H); 5.75 and 5.08 (2 m, vinyl, 3 H).

EXAMPLE 28

Synthesis of Methyl 5-(benzyl[cyano]methyl)-1-(2'-deoxy- 3,5-di-O-p-toluoyl-β-D-erythro-pentofuranosyl)imidazole-4-carboxylate A solution of methyl 5-(cyanomethyl)-1-(2'-deoxy-3,5-di-O-p-toluoyl-β-D-erythro-pentofuranosyl) imidazole-4-carboxylate (5.0 g, 9.6 mmol) in anhydrous acetonitrile (75 mL) was treated with sodium hydride (0.46 g, 11 mmol) under argon and stirred at room temperature for 15 minutes. The mixture was cooled to 4° C. in an ice bath and a solution of benzyl bromide (1.26 mL, 10.6 mmol) in acetonitrile (15 mL) was added dropwise over 70 min. The ice bath was removed and the reaction further stirred at room temperature for 2.5 hours. Workup of the reaction and purification of the products on silica gel (100 g) afforded methyl 5-(benzyl[cyano]methyl)-1-(2'-deoxy-3,5-di-O-p-toluoyl-β-D-erythro-pentofuranosyl)imidazole-4-carboxylate. as a white foam, 3.4 g (58%). 1H-NMR (Me$_2$SO-d6): δ, 8.10 and 8.05 (s,s; C-2 H, 1 H); 7.30–7.10 (m, phenyl, 5 H); 5.33 and 6.01 (t,t; H-1', 1 H).

EXAMPLE 29

Synthesis of 5-(Cyano[nonyl]methyl)-1-(2'-deoxy-β-D-erythropento-furanosyl)imidazole-4-carboxamide The nonyl-imidazole nucleoside, methyl 5-(cyano[nonyl]methyl)-1-(2'-deoxy-3,5-di-O-p-toluoyl-β-D-erythro-pentofuranosyl)imidazole-4-carboxylate, (2.98 g, 4.6 mmol) was dissolved in anhydrous methanol (5 mL) and transferred to a stainless steel bomb. The solution was cooled in a dry-ice/isopropanol bath and then treated with anhydrous liquid ammonia (45 mL). The bomb was sealed and then heated to 100° C. in an oil bath for 21 hours. TLC (ethyl acetate/methanol, 4:1, v/v) indicated a complete removal of the toluoyl protecting groups. Excess ammonia was evaporated at room temperature and the amber gum which resulted was flash chromatographed on silica gel (80 g) using ethyl acetate/methanol (95:5 then 9:1). Fractions corresponding to deblocked products were pooled and evaporated in vacuo to yield 5-(cyano[nonyl]methyl)-1-( 2'-deoxy-β-D-erythropento-furanosyl)imidazole-4-carboxamide as a white foam, 1.14 g (63%). 1H-NMR (Me$_2$SO-d6): δ, 8.09 and 8.05 (s,s; C-2 H, 1 H); 6.14 (t, H-1', 1H); 1.40–1.05 and 0.95 (2 m, nonyl, 19 H).

EXAMPLE 30

Synthesis of 5-(Allyl[cyano]methyl)-1-(2'-deoxy-β-D-erythropento-furanosyl)imidazole-4-carboxamide The allyl-imidazole nucleoside methyl 5-(allyl[cyano]methyl)-1-(2'-deoxy-3,5-di-O-p-toluoyl-8-D-erythro-pentofuranosyl)imidazole-4-carboxylate (3.95 g, 7.08 mmol) was treated with liquid ammonia in a stainless steel bomb and heated to 100° C. for 8 hours. The products of this reaction were worked up and purified on silica gel (80 g) in a manner analogous to that for compound synthesized according to Example 32, 5-(Cyano[nonyl]methyl)-1-(2'-deoxy-β-D-erythropento-furanosyl)imidazole-4-carboxamide. The de-blocked compound synthesized according to Example 33, 5-(Allyl[cyano]methyl)-1-(2'-deoxy-β-D-erythropento-furanosyl)imidazole-4-carboxamide, was isolated as a white foam, 1.29 g (58%). 1H-NMR (Me$_2$SO-d6): δ, 8.09 and 8.07 (s,s; C-2 H, 1 H); 6.15 (t, H-1', 1 H); 5.75 and 5.10 (2 m, vinyl, 3 H).

EXAMPLE 31

Synthesis of 5-(Benzyl[cyano]methyl)-1-(2'-deoxy-β-D-erythropento-furanosyl)imidazole-4-carboxamide The benzyl-imidazole nucleoside synthesized according to Example 31 (3.0 g, 4.93 mmol) was treated with liquid ammonia in a stainless steel bomb and heated to 100° C. for 6 hours. The products of this reaction were worked up and purified on silica gel (80 g) in a manner analogous to that for compound synthesized according to Example 32. The deblocked compound synthesized according to Example 34 was isolated as a white foam, 1.03 g (59%). 1H-NMR (Me$_2$SO-d6): δ, 8.03 and 8.04 (s,s; C-2 H, 1 H); 7.25 (m, phenyl, 5 H); 6.17 and 6.07 (t,t; H-1', 1 H).

EXAMPLE 32

Synthesis of 5-(Cyanomethyl)-1-(2'-deoxy-5'-O-dimethoxytrityl-β-D-orythropentofuranosyl)imidazole-4-carboxamide The nucleoside, methyl 5-(cyanomethyl)-1-(2'-deoxy-3,5-di-O-p-toluoyl-β-D-erythro-pentofuranosyl)imidazole-4-carboxamide, (1.95 g, 7.3 mmol) was dried by co-evaporation with pyridine (30 mL). The gum which resulted was dissolved in anhydrous pyridine under argon and then treated with dimethoxytrityl chloride (2.90 g, 12.4 mmol). The mixture was stirred at room temperature for 2 hours after which TLC (ethyl acetate:methanol, 19:1, v/v) indicated complete conversion of starting material. Tritylated products were visualized as orange spots using H$_2$SO$_4$ fumes.

The reaction was quenched with the addition of methanol (2 mL) followed by stirring for 15 min. The mixture was evaporated in vacuo to afford a thick orange syrup which was co-evaporated with toluene (3×25 mL). The syrup was flash chromatographed on silica gel (100 g) using a stepwise gradient of methanol in 1% Et$_3$N/CH$_2$Cl$_2$ (0 to 5% methanol). The appropriate fractions were pooled and evaporated to yield 5-(Cyanomethyl)-1-(2'-deoxy-5'-O-dimethoxytrityl-β-D-erythropentofuranosyl)imidazole-4-carboxamide as a white foam, 3.64 g (87%). 1H-NMR (Me$_2$SO-d6): δ, 7.96 (s, C-2 H, 1 H); 6.85–7.35 (m, DMT, 13 H); 6.13 (t, H-1', 1 H).

EXAMPLE 33

Synthesis of 5-(Cyano[nonyl]methyl)-1-(2'-deoxy-5'-O-dimethoxytrityl-β-D-orythropentofuranosyl)imidazole-4-carboxamide The nucleoside synthesized according to Example 32 (1.20 g, 3.1 mmol) was thoroughly dried by co-evaporation with anhydrous pyridine (30 mL). The syrup which resulted was redissolved in anhydrous pyridine under argon and treated with dimethoxytrityl chloride (1.0 g, 3.1 mMol). The reaction mixture was stirred at room temperature for 3.5 hr, after which time TLC (ethyl acetate) indicated complete conversion of the starting material. The reaction mixture was treated with 2 mL of anhydrous methanol, stirred for 15 minutes and then evaporated in vacuo to afford a bright orange syrup. This syrup was co-evaporated with toluene (2×50 mL) and then flash chromatographed on silica (80 g) using a step-wise gradient of methanol in dichloromethane/1% triethylamine (0 to 3% methanol). The appropriate fractions were pooled and evaporated in vacuo to yield the dimethoxytritylated compound 5-(Cyano[nonyl]methyl)-1-(2'-deoxy-5'-O-dimethoxytrityl-β-D-erythropentofuranosyl)imidazole-4-carboxamide as a white foam, 1.46 g (69%). 1H-NMR (Me$_2$SO-d6): δ, 7.98 and 7.93 (s,s; C-2 H, 1 H); 7.30 and 6.92 (2 m, DMT, 13 H); 6.21 (t, H-1', 1 H); 1.20 and 0.92 (2 m, nonyl, 19 H).

EXAMPLE 34

Synthesis of 5-(Allyl[cyano]methyl)-1-(2'-deoxy-5'-O-dimethoxytrityl-β-D-erythropentofuranosyl)imidazole-4-carboxamide The nucleoside synthesized according to Example 33 (1.25 g, 4.08 mmol) was dried by co-evaporation with pyridine and then redissolved in anhydrous pyridine (50 mL) and treated with dimethoxy-trityl chloride (1.38 g, 4.08 mmol) under an atmosphere of argon. The reaction was stirred for 2.5 hours and then worked up and products isolated by flash chromatography on silica gel (90 g) in a manner analogous to compound synthesized according to Example 35. The appropriate fractions were pooled and evaporated in vacuo to yield dimethoxytritylated compound 37 as a white foam, 1.86 g (75%). 1H-NMR (Me$_2$SO-d6): δ, 7.98 and 7.95 (s,s; C-2 H, 1 H); 7.25 and 6.93 (2 m, DMT, 13 H); 6.21 (m, H-1', 1 H); 5.78 and 5.10 (2 m, vinyl, 3 H).

EXAMPLE 35

Synthesis of 5-(Benzyl[cyano]methyl)-1-(2'-deoxy-5'-O-dimethoxy-trityl-β-D-erythropentofuranosyl) imidazole-4-carboxamide The nucleoside synthesized according to Example 34, 930 mg (2.6 mmol) was dried by co-evaporation with pyridine and then redissolved in anhydrous pyridine (50 mL) and treated with dimethoxy-trityl chloride (884 mg, 2.6 mmol) under an atmosphere of argon. The reaction was stirred for 4 hours and then worked up and the products isolated by flash chromatography on silica gel (80 g) in a manner analogous to the compound synthesized according to Example 35. The appropriate fractions were pooled and evaporated in vacuo to yield 1.50 g of 5-(Benzyl[cyano]methyl)-1-(2'-deoxy-5'-O-dimethoxy-trityl-β-D-erythropentofuranosyl)imidazole-4-carboxamide as a pinkish foam, (87%). 1H-NMR (Me$_2$SO-d6): δ, 7.70 (s, C-2 H, 1 H); 7.40 and 6.70 (2m; DMT, phenyl;18 H);

6.10 (t, H-1', 1 H).

EXAMPLE 36

Synthesis of 5-(Cyanomethyl)-1-(5'-O-dimethoxytrityl-3'-O-[2-cyano-ethyl-N,N-diisopropyl]phosphoramidite-2'-deoxy-β-D-erythropentofuranosyl)imidazole-4-carboxamide The tritylated nucleoside synthesized according to Example 35 (1.82 g, 3.2 mmol) was dissolved in anhydrous tetrahydrofuran (50 mL) under argon and then treated with diisopropyl ethylamine (1 mL). The solution was cooled to 4° C. in an ice bath and then treated with 2-cyanoethyl-N,N-diisopropyl phosphorochloridate (1.2 g, 5.12 mmol) in one portion. The ice bath was removed and the reaction mixture was stirred at room temperature for 3 hours. At the end of this time, TLC (CH$_2$Cl$_2$/1% MeOH/1% Et$_3$N) indicated complete conversion of starting material. Reaction products were visualized using H$_2$SO$_4$ fumes. The reaction mixture was evaporated in vacuo to afford a thick syrup which was immediately redissolved in dichloromethane (100 mL) and washed with cold, saturated sodium bicarbonate (2×50 mL) and brine (50 mL). The organic layer was dried over magnesium sulfate, filtered and evaporated to yield a yellowish foam (2.8 g). This foam was flash chromatographed on silica gel (75 g) using a stepwise gradient of ethyl acetate/hexanes (1:4 to 1:1) containing 1% Et$_3$N. The appropriate fractions were pooled and evaporated to yield 5-(Cyanomethyl)-1-(5'-O-dimethoxytrityl-3'-O-[2-cyanoethyl-N,N-diisopropyl]phosphoramidite-2'-deoxy-β-D-erythropentofuranosyl)imidazole-4-carboxamide. as a white foam, 1.65 g (59%). An aliquot of this material was precipitated by dissolving the foam in a small volume of dichloromethane and adding it to a large proportion (1:50) of hexanes. 1H-NMR (CD$_3$CN): δ, 7.78 and 7.72 (s,s; C-2 H, 1H); 7.25 and 6.95 (m, DMT, 13 H); 6.12 (t, H-1', 1H). 31P-NMR (CD$_3$CN): δ, 150.02, 149.98.

EXAMPLE 37

Synthesis of 5-(Cyano[nonyl]methyl)-1-(5'-O-dimethoxytrityl-3'-O-[2-cyanoethyl-N,N-diisopropyl]phosphoramidite-2'-deoxy-B-D-erythropentofuranosyl)imidazole-4-carboxamide The tritylated nucleoside synthesized according to Example 36, 1.46 g (2.1 mmol) was dissolved in anhydrous tetrahydrofuran (50 mL) under argon and then treated with diisopropyl ethylamine (1.5 mL). This mixture was cooled to 4° C. in an ice bath and then treated with 2-cyanoethyl-N,N-diisopropylamino phosphorochloridite (488 mg, 2.1 mmol) in one portion. The ice bath was removed and the reaction was further stirred at room temperature for a total of 3 hours. Additional phosphorochloridite (48 mg) was added at the end of the first and second hours of reaction. At the end of this time, TLC (CH$_2$Cl$_2$/3% MeOH/1% Et$_3$N) indicated complete conversion of starting material. The reaction mixture was worked up as described for the compound synthesized according to Example 39 and the products purified on silica gel (80 g) using a stepwise gradient of ethyl acetate/hexanes (2:3 to 3:2) containing 1% Et$_3$N. The appropriate fractions were pooled and evaporated to afford 5-(Cyano[nonyl]methyl)-1-(5'-O-dimethoxytrityl-3'-O-[2-cyanoethyl-N,N-diisopropyl]phosphoramidite-2'-deoxy-β-D-erythropentofuranosyl)imidazole-4-carboxamide as a colorless foam, 1.37 g (73%). An aliquot of this material was precipitated using a procedure described for the compound synthesized according to Example 39. 1H-NMR (CD$_3$CN): δ, 7.75 (s, C-2 H); 7.25 and 6.85 (2 m, DMT, 13 H), 6.25 and 6.20 (2 m, H-1', 1 H). $^{31}$P-NMR (CD$_3$CN): δ, 150.1, 150.0 and 149.9.

EXAMPLE 38

Synthesis of 5-(Ally[cyano]methyl)-1-(5'-O-dimethoxytrityl-3'-O-[2-cyanoethyl-N,N-diisopropyl]phosphoramidits-2'-deoxy-β-D-erythropentofuranosyl)imidazole-4-carboxamide The tritylated nucleoside synthesized according to Example 37, 1.86 g (3.1 mmol) was dissolved in anhydrous THF (50 mL) and then treated with diisopropyl ethylamine (1.5 mL) and 2-cyanoethyl N,N-diisopropylamino phosphochloridite (705 mg, 3.1 mmol) in a manner analogous to the compound synthesized according to Example 40. The mixture was stirred at room temperature for a total of 3 hours. Additional phosphochloridite (140 mg) was added at the end of 2 hour reaction time. The reaction was worked up and the products isolated by flash chromatography on silica gel (80 g) using a stepwise gradient of ethyl acetate/hexanes (2:3 to 4:1, v/v). The appropriate fractions were pooled and evaporated to yield 2.18 g (88%) of 41 as a white solid foam. An aliquot of this material was precipitated using a procedure described for compound synthesized according to Example 39. 1H-NMR (CD$_3$CN): δ, 7.77 and 7.75 (s,s; C-2 H, 1 H); 7.45 and 6.85 (2m, DMT, 13 H); 6.25 and 6.20 (t,t; H-1', 1 H). 31P-NMR (CD$_3$CN): δ, 150.05, 149.98 and 149.85.

EXAMPLE 39

Synthesis of 5-(Benzyl[cyano]methyl)-1-(5'-O-dimethosytrityl-3'-O-[2-cyanoethyl-N,N-diisopropyl]phosphoramidite-2'-deoxy-β-D-erythropentofuranosyl)imidazole-4-carboxamide The tritylated nucleoside synthesized according to Example 38, 1.50 g (2.3 mmol) was dissolved in anhydrous THF (50 mL) and then treated with diisopropyl ethylamine (1.5 mL) and 2-cyanoethyl-N,N-di-isopropylamino phosphochloridite (539 mg, 2.3 mmol) in a manner analogous to the compound synthesized according to Example 39. The mixture was stirred at room temperature for a total of 3 hours. Additional phosphorochloridite (110 mg) was added at the end of 2 hours reaction time. The reaction was worked up and the products isolated by flash chromatography on silica gel (40 g) using a stepwise gradient of ethyl acetate/hexanes (1:4 to 3:2, v/v). The appropriate fractions were pooled and evaporated to yield 5-(Benzyl[cyano]methyl)-1-(5'-O-dimethoxytrityl-3'-O-[2-cyanoethyl-N,N-diisopropyl] phosphoramidite-2'-deoxy-β-D-erythro-pentofuranosyl) imidazole-4-carboxamide., 1.03 g (55%) as a colorless foam. An aliquot of this material was precipitated using a procedure described for the compound synthesized according to Example 39. 1H-NMR (CD$_3$CN): δ, 7.72 (s,s; C-2 H; 1 H); 7.30 and 6.80 (2 m; DMT, benzyl; 18 H); 6.10 (m, H-1', 1 H). $^{31}$P-NMR (CD$_3$CN): δ, 150.00, 149.90 and 149.85.

EXAMPLE 40

Synthesis of Oligomers

Oligomers incorporating the nucleotides of Examples 39, 40, 41 and 42 were made using standard phorphoramidite chemistries on an Applied Biosystems 380B synthesizer. Average coupling efficiencies were 94% using a method which left the 5'-dimethoxytrityl group of each oligonucleotide on. After cleavage from the solid support, the oligomers were treated with excess concentrated ammonium hydroxide and then heated in a sealed vessel at 55° C. for a minimum of 15 hours. This procedure removed all protecting groups from A, G and C bases and caused cyclization of the 5-cyano[alkyl]methyl imidazole to the 3-deaza-3-alkyl (or aryl) heterocycles. For each nucleotide, verification of this cyclization was made from the analysis of a 1H-NMR spectrum of a TG3C trimer containing a single 3-deaza-3-substituted 2'-deoxyguanosine base. Purification of these trityl-on oligomers was performed using a C-4 Waters Prepak cartridge (10 cm) using a gradient elution of acetonitrile in 50 mM triethyl ammonium acetate (pH 7.0) (4 to 48% over 60 min). The trityl group was removed by a treatment with 15% acetic acid and the oligomers were then precipitated from 70% ethanol.

EXAMPLE 41

Synthesis of 5-(Cyano[propylphthalimide]methyl)-1-(5'-O-dimethoxy-trityl-3'-O'[2-cyanoethyl-N,N-diisopropyl]phosphoramidite-2'-deoxy-β-D-erythro-pentofuranosyl-imidazole-4-carboxamide In a manner as per Example 29, the compound methyl 5-(cyanomethyl)-1-(2'-deoxy-3,5-di-O-p-toluoyl-β-D-erythro-pentofuranosyl)imidazole-4-carboxylate can be treated with N-(3-bromopropyl)phthalimide instead of iodononane. After work-up as per Example 29 the product can be treated as per Examples 35 and 39 to yield the 5-(Cyano[propylphthalimide]methyl)-1-(5'-O-dimethoxy-trityl-3'-O'[2-cyanoethyl-N,N-diisopropyl] phosphoramidite-2'-deoxy-β-D-erythro-pentofuranosyl-imidazole-4-carboxamide. In addition to ring closure upon cleavage from the oligonucleotide synthesizer solid support, the phthalimide is also cleaved to amino as per other above examples. Further the alkylamino product can be chain extended to a polyalkylamine.

EXAMPLE 42

Synthesis of 5-(Cyano[imidizo-1-yl(propyl)] methyl)-1-(5'-O-dimethoxy-trityl-3'-O'[2-cyanoethyl-N,N-diisopropyl]phosphor-amidite-2'-deoxy-β-D-erythro-pentofuranosyl-imidazole-4-carboxamide In a manner as per Example 29, the compound methyl 5-(cyanomethyl)-1-(2'-deoxy-3,5-di-O-p-toluoyl-β-D-erythro-pentofuranosyl)imidazole-4-carboxylate can be treated with 1-(3-bromopropyl)imidazole instead of iodononane. After work-up as per Example 29 the product can be treated as per Examples 35 and 39 to yield 5-(Cyano [imidizo-1-yl(propyl)]methyl)-1-(5'-O-dimethoxy-trityl-3'-O'[2-cyanoethyl-N,N-diisopropyl]phosphoramidite-2'-deoxy-β-D-erythro-pentofuranosyl-imidazole-4-carboxamide.

EXAMPLE 43

Synthesis of 5-(Cyano[anthracen-2-yl(propyl)] methyl)-1-(5'-O-di-methoxy-trityl-3'-O'[2-cyanoethyl-N,N-diisopropyl]phosphoramidite- 2'-deoxy-β-D-erythro-pentofuranosyl-imidazole-4-carboxamide In a manner as per Example 29, the compound methyl 5-(cyanomethyl)-1-(2'-deoxy-3,5-di-O-p-toluoyl-β-D-erythro-pentofuranosyl)imidazole-4-carboxylate can be treated with 2-(3-bromopropyl)anthracene instead of iodononane. After work-up as per Example 29 the product can be treated as per Examples 35 and 39 to yield 5-(Cyano [anthracen-2-yl(propyl)]methyl)-1-(5'-O-di-methoxy-trityl-3'-O'[2-cyanoethyl-N,N-diisopropyl]phosphoramidite-2'-deoxy-β-D-erythro-pentofuranosyl-imidazole-4-carboxamide.

What is claimed is:

1. A nucleoside having the formula:

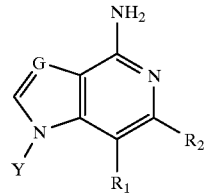

wherein G is CH or N; $R_1$ is $NH_2$, alkyl having from one to about 12 carbons, substituted alkyl having from one to about 12 carbons, alkenyl having from 2 to about 12 carbons, substituted alkenyl having from 2 to about 12 carbons, aralkyl having from about 6 to about 30 carbons, or amino, $R_2$ is amino, alkyl having from 1 about 12 carbons, substituted alkyl having from 1 about 12 carbons, alkenyl having from 2 to about 12 carbons, substituted alkenyl having from 2 to about 12 carbons, or aralkyl having from about 6 to about 30 carbons; and Y is a sugar having an activated phosphate group.

2. The compound of claim 1 wherein said sugar is ribose or deoxyribose.

3. The compound of claim 2 wherein $R_2$ is amino.

4. The compound of claim 2 wherein said activated phosphorus group is a phosphoramidite group.

5. The compound of claim 1 wherein $R_1$ is alkenyl having up to about 12 carbon atoms.

6. The compound of claim 1 wherein $R_1$ is aralkyl having from about 6 to about 30 carbon atoms.

7. The compound of claim 2 wherein $R_1$ is alkyl having up to about 12 carbon atoms.

8. The compound of claim 2 wherein $R_1$ is alkenyl having up to about 12 carbon atoms.

9. The compound of claim 2 wherein $R_1$ is aralkyl having from about 6 to about 30 carbon atoms.

10. The compound of claim 1 wherein G is N; $R_1$ is alkyl; $R_2$ is amino; and said sugar is ribose or deoxyribose.

11. The compound of claim 1 wherein G is N; $R_1$ is alkenyl; $R_2$ is amino; and said sugar is ribose or deoxyribose.

12. The compound of claim 1 wherein G is N; $R_1$ is aralkyl; $R_2$ is amino; and said sugar is ribose or deoxyribose.

13. The compound of claim 1 wherein G is N; $R_1$ is 1-methyl octane, 1-propene, phenyl methyl, or naphthylmethyl; $R_2$ is amino; and said sugar is ribose or deoxyribose.

14. A compound having the formula:

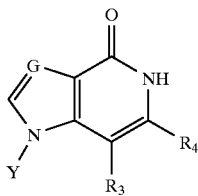

wherein G is CH or N; $R_3$ is H, $NH_2$, alkyl having 1 to about 12 carbons, substituted alkyl having 1 to about 12 carbons, alkenyl having from 2 to about 12 carbons, substituted alkenyl having from 2 to about 12 carbons, aralkyl having from about 6 to about 30 carbons, or amino; $R_4$ is $NH_2$, alkyl having 1 to about 12 carbons, substituted alkyl having 1 to about 12 carbons, alkenyl having from 2 to about 12 carbons, substituted alkenyl having from 2 to about 12 carbons, aralkyl having from about 6 to about 30 carbons, or amino; and Y is a sugar having an activated phosphate group; provided that when $R_3$ is H, $R_4$ is not $NH_2$.

15. The compound of claim 14 wherein said sugar is ribose or deoxyribose.

16. The compound of claim 14 wherein said activated phosphorus group is a phosphoramidite group.

17. The compound of claim 14 wherein $R_3$ is alkenyl having up to about 12 carbon atoms.

18. The compound of claim 14 wherein $R_3$ is aralkyl having from about 6 to about 30 carbon atoms.

19. The compound of claim 16 wherein $R_3$ is alkyl having up to about 12 carbon atoms.

20. The compound of claim 15 wherein $R_3$ is alkenyl having up to about 12 carbon atoms.

21. The compound of claim 15 wherein $R_3$ is aralkyl having up to about 6 to 30 carbon atoms.

22. The compound of claim 15 wherein G is N; $R_3$ is alkyl; $R_4$ is $NH_2$; and said sugar is ribose or deoxyribose.

23. The compound of claim 14 wherein G is N; $R_3$ is alkenyl; $R_4$ is $NH_2$; and said sugar is ribose or deoxyribose.

24. The compound of claim 14 wherein G is N; $R_3$ is aralkyl; $R_4$ is $NH_2$; and said sugar is ribose or deoxyribose.

25. The compound of claim 14 wherein G is N; $R_3$ is 1-methyl octane, 1-propene, phenyl methyl, or naphthylmethyl; $R_4$ is $NH_2$; and said sugar is ribose or deoxyribose.

* * * * *

UNITED STATES PATENT AND TRADEMARK OFFICE
CERTIFICATE OF CORRECTION

PATENT NO.   : 5,948,903
DATED        : September 7, 1999
INVENTOR(S)  : Cook et al.

It is certified that error appears in the above-identified patent and that said Letters Patent is hereby corrected as shown below:

Title page,
Item [60], Related U.S. Application Data, please delete "5,380,429" and insert therefor -- 5,457,191 --;

Column 3,
Line 55, delete "oli" and insert therefor -- Oli --;

Columns 17-18,
Delete last compound and insert therefor

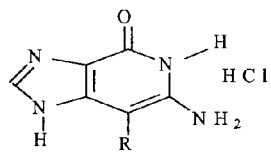

Column 18,
Line 55, delete "D" and insert therefor -- β --;

Column 21,
Line 6, delete "nay" and insert therefor -- any --;
Line 61, delete "[2,3-]" and insert therefor -- [2,3-β] --;

Column 22,
Line 11, delete "oligonucleotides" and insert therefor -- Oligonucleotides --;
Line 44, delete "oligonucleotides" and insert therefor -- Oligonucleotides --;

Column 23,
Line 20, delete "oligonucleotides" and insert therefor -- Oligonucleotides --;
Line 29, delete "inlcude" and insert therefor -- include --;

Column 24,
Line 29, delete "100" and insert therefor -- 100 --;

Column 29,
Line 43, delete "λmax,nm" and insert therefor -- λmax,nm --;

Column 32,
Line 10, delete "carboaylate" and insert therefor -- carboxylate --;

Column 33,
Line 40, delete "8" and substitute therefor -- β --;

UNITED STATES PATENT AND TRADEMARK OFFICE
CERTIFICATE OF CORRECTION

PATENT NO. : 5,948,903
DATED : September 7, 1999
INVENTOR(S) : Cook et al.

It is certified that error appears in the above-identified patent and that said Letters Patent is hereby corrected as shown below:

Column 34,
Line 8, delete "orythropentofuranosyl" and substitute therefor -- erythropentofuranosyl --;
Line 36, delete "orythropentofuranosyl" and substitute therefor -- erythropentofuranosyl --;

Column 36,
Line 7, delete "B" and substitute therefor -- β --;
Line 63, delete "dimethosytrityl" and substitute therefor -- dimethoxytrityl --;

Column 39,
Lines 4-5, delete "naphthylmethyl" and substitute therefor -- napthylethyl --;

Column 40,
Line 22, delete "naphthylmethyl" and substitute therefor -- napthylethyl --.

Signed and Sealed this

Fifteenth Day of October, 2002

Attest:

Attesting Officer

JAMES E. ROGAN
*Director of the United States Patent and Trademark Office*